(12) United States Patent
Komuro et al.

(10) Patent No.: US 6,501,545 B2
(45) Date of Patent: Dec. 31, 2002

(54) DEFECT DETECTING APPARATUS

(75) Inventors: Takahiro Komuro, Kamiina-gun (JP); Haruyuki Tsuji, Ina (JP); Yasutada Miura, Hachioji (JP); Toshihiko Tanaka, Komagane (JP)

(73) Assignee: Olympus Optical Co., Ltd., Tokyo (JP)

(*) Notice: Subject to any disclaimer, the term of this patent is extended or adjusted under 35 U.S.C. 154(b) by 0 days.

(21) Appl. No.: 09/989,923

(22) Filed: Nov. 21, 2001

(65) Prior Publication Data

US 2002/0031249 A1 Mar. 14, 2002

Related U.S. Application Data

(63) Continuation of application No. PCT/JP01/02369, filed on Mar. 23, 2001.

(30) Foreign Application Priority Data

Mar. 24, 2000 (JP) ........................................ 2000-083409
Sep. 1, 2000 (JP) ........................................ 2000-265737

(51) Int. Cl.[7] .............................................. G01N 21/00
(52) U.S. Cl. ............................ 356/237.2; 356/237.5; 356/630
(58) Field of Search .......................... 356/237.1, 237.2, 356/237.3, 237.4, 237.5, 394, 630, 631, 632; 250/559.27, 559.4, 559.42, 559.41; 348/125, 126, 128

(56) References Cited

U.S. PATENT DOCUMENTS 5,086,232 A * 2/1992 Maguire et al. ............ 250/572
5,963,328 A * 10/1999 Yoshida et al. .......... 356/237.2
6,097,482 A1 * 8/2001 Smith et al. ............. 356/237.1

FOREIGN PATENT DOCUMENTS

| JP | 8-264605 | 10/1996 |
|----|----------|---------|
| JP | 9-61365 | 3/1997 |
| JP | 10-339701 | 12/1998 |
| JP | 11-6803 | 1/1999 |
| JP | 11-72443 | 3/1999 |
| JP | 11-166901 | 6/1999 |

* cited by examiner

Primary Examiner—Hoa Q. Pham
(74) Attorney, Agent, or Firm—Frishauf, Holtz, Goodman & Chick, P.C.

(57) ABSTRACT

A defect detecting apparatus comprising an illuminating unit which irradiates an object with illumination an image sensing unit which senses an image of the object an angle controller which controls an inclination angle of at least one of the illuminating unit and the image sensing unit, an image processor which senses images of the object while the angle controller changes the inclination angle of at least one of the illuminating unit and the image sensing unit and obtains a relationship between each inclination angle and optical information corresponding to the each inclination angle, and a determination unit which determines an image sensing condition suited to observation in accordance with the relationship wherein the angle controller sets the inclination angle of the illuminating unit or the image sensing unit on the basis of a determination result from the determination unit such that the inclination angle matches the image sensing condition.

28 Claims, 17 Drawing Sheets

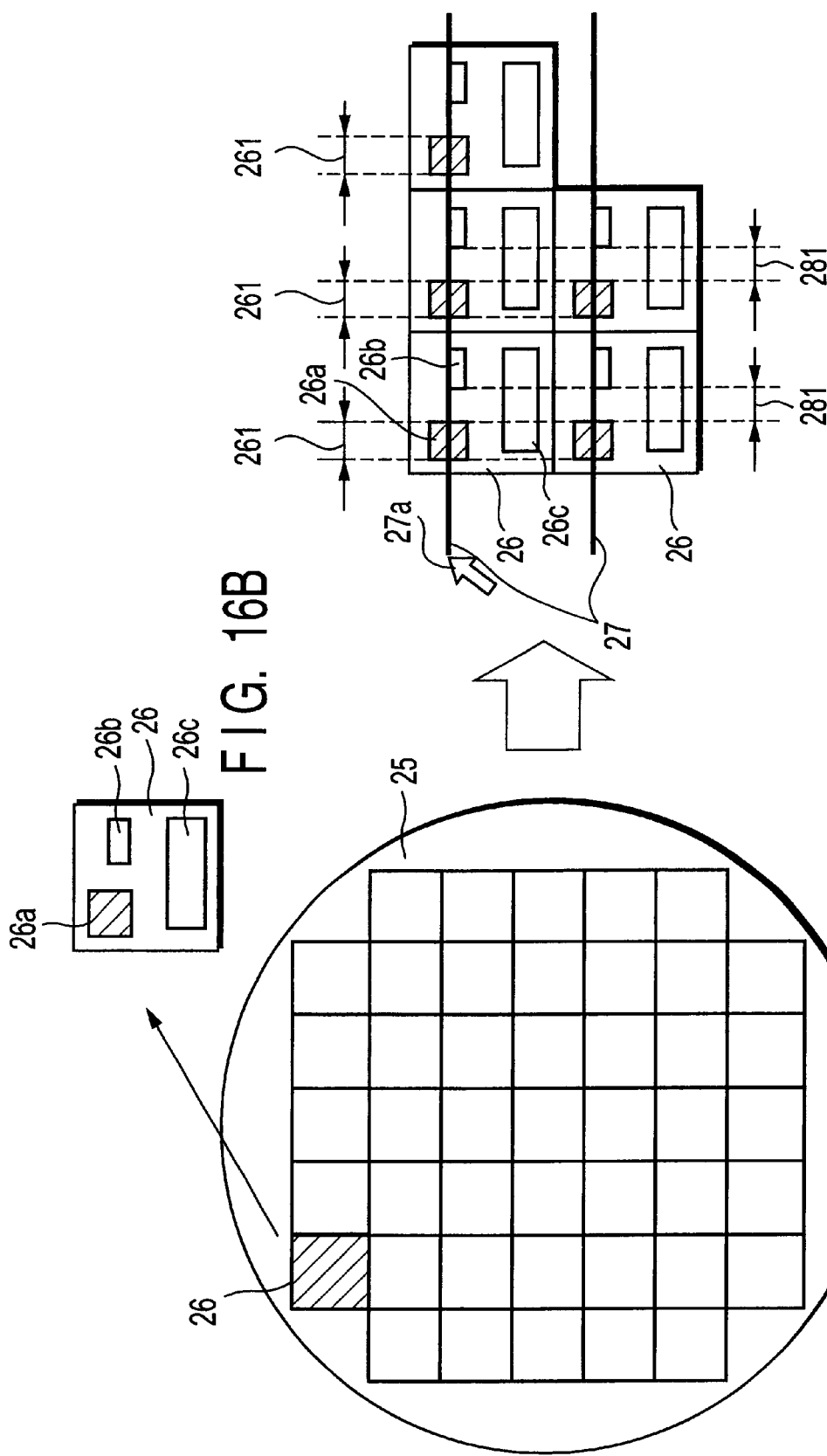

DEFECT DETECTING APPARATUS

CROSS-REFERENCE TO RELATED APPLICATIONS

This is a Continuation Application of PCT Application No. PCT/JP01/02369, filed Mar. 23, 2001, which was not published under PCT Article 21(2) in English.

This application is based upon and claims the benefit of priority from the prior Japanese Patent Applications No. 2000-083409, filed Mar. 24, 2000; No. 2000-265737, filed Sep. 1, 2000, the entire contents of both of which are incorporated herein by reference.

BACKGROUND OF THE INVENTION

1. Field of the Invention

The present invention relates to a defect detecting apparatus for detecting macroscopic defects such as film thickness variations, contamination, pattern steps, and flaws on the surface of a semiconductor wafer substrate or a liquid crystal glass substrate.

2. Description of the Related Art

A surface defect detecting apparatus disclosed in Jpn. Pat. Appln. KOKAI Publication No. 9-61365 is a conventional apparatus for automatically inspecting substrates such as semiconductor wafer substrates and liquid crystal glass substrates. This apparatus illuminates the surface of an object to be detected and senses images of the regularly reflected light, diffracted light, and scattered light from the surface. In this way, the apparatus can detect film thickness variations, periodic disturbance of resist patterns, differences in sectional shape between resist steps, and the like by image processing. However, the surface defect detecting apparatus having this arrangement does not automatically optimize the angle of illumination and the like when sensing an image of the diffracted light. This makes defect inspection in an optimum state difficult to perform.

On the other hand, a method of automatically adjusting illumination for sensing an image of the diffracted light from a substrate such as a semiconductor wafer substrate or a liquid crystal glass substrate has been proposed. For example, a defect inspecting apparatus disclosed in Jpn. Pat. Appln. KOKAI Publication No. 10-339701 reads information concerning a pattern formed on a substrate, and checks whether the pattern is a periodic pattern. If the pattern is a periodic pattern, the apparatus receives the diffracted light and proceeds on to inspection. If the pattern is a line-and-space pattern, for example, the apparatus sets a rotational angle around the normal of the surface of the substrate such that the line direction is perpendicular to the incident direction of illuminating light. The apparatus calculates a diffraction angle $\theta d$ to the pattern pitch by an equation: $\sin \theta d - \sin \theta i = m\lambda/p$, and sets the diffraction angle $\theta d$ obtained by this calculation as the angle of light reception.

However, in the apparatus which automatically adjusts illumination when sensing an image of the diffracted light as described above, the movement of an illuminating optical system is limited to a narrow range, so the incident direction of the illuminating light cannot be easily changed. Since this limits patterns which can be inspected by this apparatus, the apparatus cannot treat objects having various patterns.

Also, patterns formed on semiconductor wafer substrates and liquid crystal glass substrates are complicated, and have not only a kind of pattern pitch but also differ in pattern pitch according to portions on the substrate. Therefore, a good diffracted image cannot be necessarily obtained by the set diffracted light receiving angle. Furthermore, an optimum diffracted light receiving angle changes in accordance with the influence of a resist on the substrate and the like.

Conventionally, defects such as film thickness variations, periodic disturbance of resist patterns, and differences in sectional shape between resist steps on a substrate such as a semiconductor wafer substrate or a liquid crystal glass substrate are inspected by sensing an interference observation image of the substrate. This interference observation image is generated by interference between reflected light from the surface of a thin film (e.g., a resist film) formed on the substrate and light transmitted through the thin film and reflected from the substrate surface when illuminating light is irradiated to the substrate. To sense this interference observation image, illuminating light is made close to a single wavelength, or a bandpass filter is inserted before an image sensing device.

When an interference observation image is to be sensed, however, the interference conditions change in accordance with the conditions of a substrate such as the thickness and refractive index of a resist film, and the wavelength (observation wavelength) of illuminating light, so image sensing may not be performed under preferred conditions. As an example, an image saturates and makes it impossible to sense an interface observation image under favored conditions. Also, an apparatus which selectively interchanges a plurality of bandpass filters to change the observation wavelength selects the wavelength step by step. That is, the apparatus does not select a wavelength for performing image sensing under preferred conditions.

It is an object of the present invention to provide a defect detecting apparatus capable of setting to an optimum state the angle of at least one of an illuminating side and an image sensing side with respect to an object to be inspected, and capable of treating various objects.

BRIEF SUMMARY OF THE INVENTION

A defect detecting apparatus for extracting a defect from image data obtained by sensing an image of an object to be inspected, comprising:

an illuminating unit which irradiates the object with illumination from a direction of predetermined angle;

an image sensing unit which senses an image of the object from the direction of predetermined angle;

an angle controller which controls an inclination angle of at least one of the illuminating unit and the image sensing unit;

an image processor which senses images of the object while the angle controller changes the inclination angle of at least one of the illuminating unit and the image sensing unit and obtains a relationship between each inclination angle and optical information corresponding to the each inclination angle; and a determination unit which determines an image sensing condition suited to observation in accordance with the relationship between the inclination angle and optical information obtained by the image processor, wherein the angle controller sets the inclination angle of the illuminating unit or the image sensing unit on the basis of a determination result from the determination unit such that the inclination angle matches the image sensing condition.

A defect detecting apparatus comprising:

an illuminating unit whose incident angle $\theta$ changes with respect to a normal to a surface of an object to be inspected;

an image sensing unit which senses an image of light reflected by the object illuminated with the illuminating unit, the image sensing unit has an image sensing angle θ changing with respect to the normal;

an image analyzer which extracts defect information from an image of the object sensed by the image sensing unit;

a determination unit which obtains an interference angle suited to interference observation on the basis of an observation wavelength and information concerning a film formed on the object; and an angle controller which controls an inclination angle of the illuminating unit sand the image sensing unit on the basis of the interference angle obtained by the determination unit.

A defect detecting apparatus comprising:

an illuminating unit whose incident angle θ changes with respect to a normal to a surface of an object to be inspected;

an image sensing unit which senses an image of light reflected by the object illuminated with the illuminating unit, the image sensing unit has an image sensing angle θ changing with respect to the normal;

an angle controller which controls the illuminating unit and the image sensing unit such that an incident angle to the object is set equal to an image sensing angle;

an image processor which causes the image sensing unit to sense an image while the inclination angle of the illumination unit and the image sensing unit is changed by the angle controller, thereby obtains a relationship of a luminance value to the inclination angle; and a determination unit which determines an optimum interference angle in accordance with the relationship of the luminance value to the inclination angle, which is obtained by the image processor, wherein the angle controller controls the inclination angle of the illuminating unit and the image sensing unit on the basis of the interference angle obtained by the determination unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 16A, 16B, and 16C are views showing a display example of an image display unit in a defect detecting apparatus according to the 11th embodiment of the present invention;

DETAILED DESCRIPTION OF THE INVENTION

Embodiments of the present invention will be described below with reference to the accompanying drawing.

Figure 1:
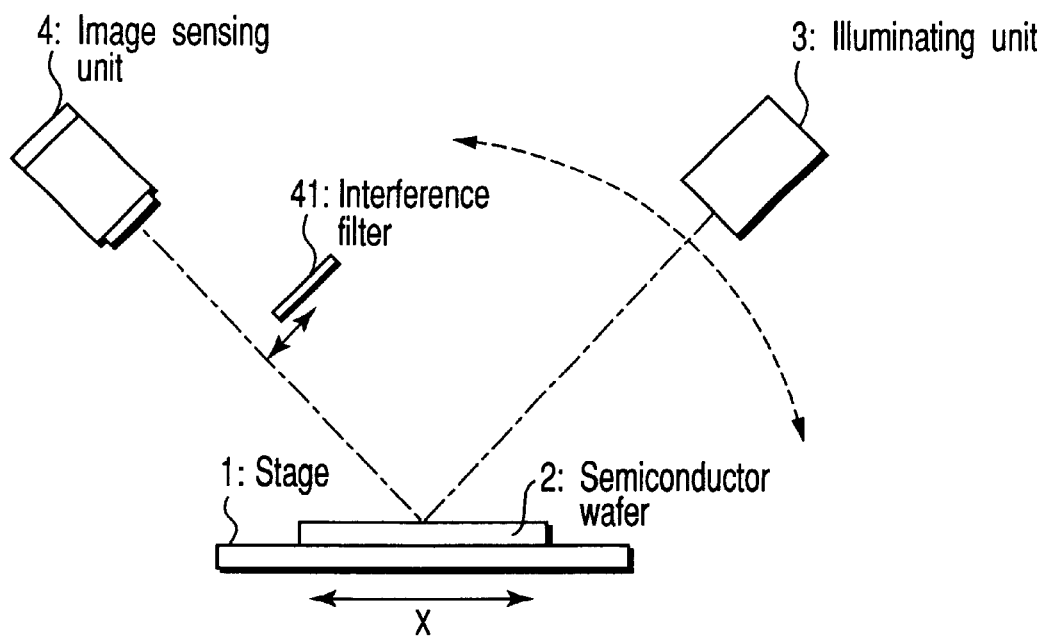
FIG. 1 is view showing an outline of the configuration of an image sensing system and illuminating system of a defect detecting apparatus according to the first embodiment of the present invention.

FIG. 1 is a view showing an outline of the configuration of an image sensing system and illuminating system of a defect detecting apparatus according to the first embodiment of the present invention. Referring to FIG. 1, a semiconductor wafer 2 as an object to be inspected is placed on a stage 1. A linear illuminating unit 3 and an image sensing unit 4 such as a line sensor camera are arranged above the stage 1. The optical axis of the illuminating unit 3 is inclined at a predetermined angle to the surface of the semiconductor wafer 2. This illuminating unit 3 irradiates the surface of the semiconductor wafer 2 with linear illuminating light. The optical axis of the image sensing unit 4 is inclined at a predetermined angle to the surface of the semiconductor wafer 2. The image sensing unit 4 senses, line by line, an image of that diffracted light from the surface of the semiconductor wafer 2, which is generated by illumination by the illuminating unit 3. Note that this image sensing unit 4 is fixed with its optical axis inclined the predetermined angle. The illuminating unit 3 can be rotated so that the inclination angle to the surface of the semiconductor wafer 2 can be adjusted within a predetermined range. This illuminating unit 3 can be fixed to a desired position by an electrical or mechanical stopper.

Figure 2:
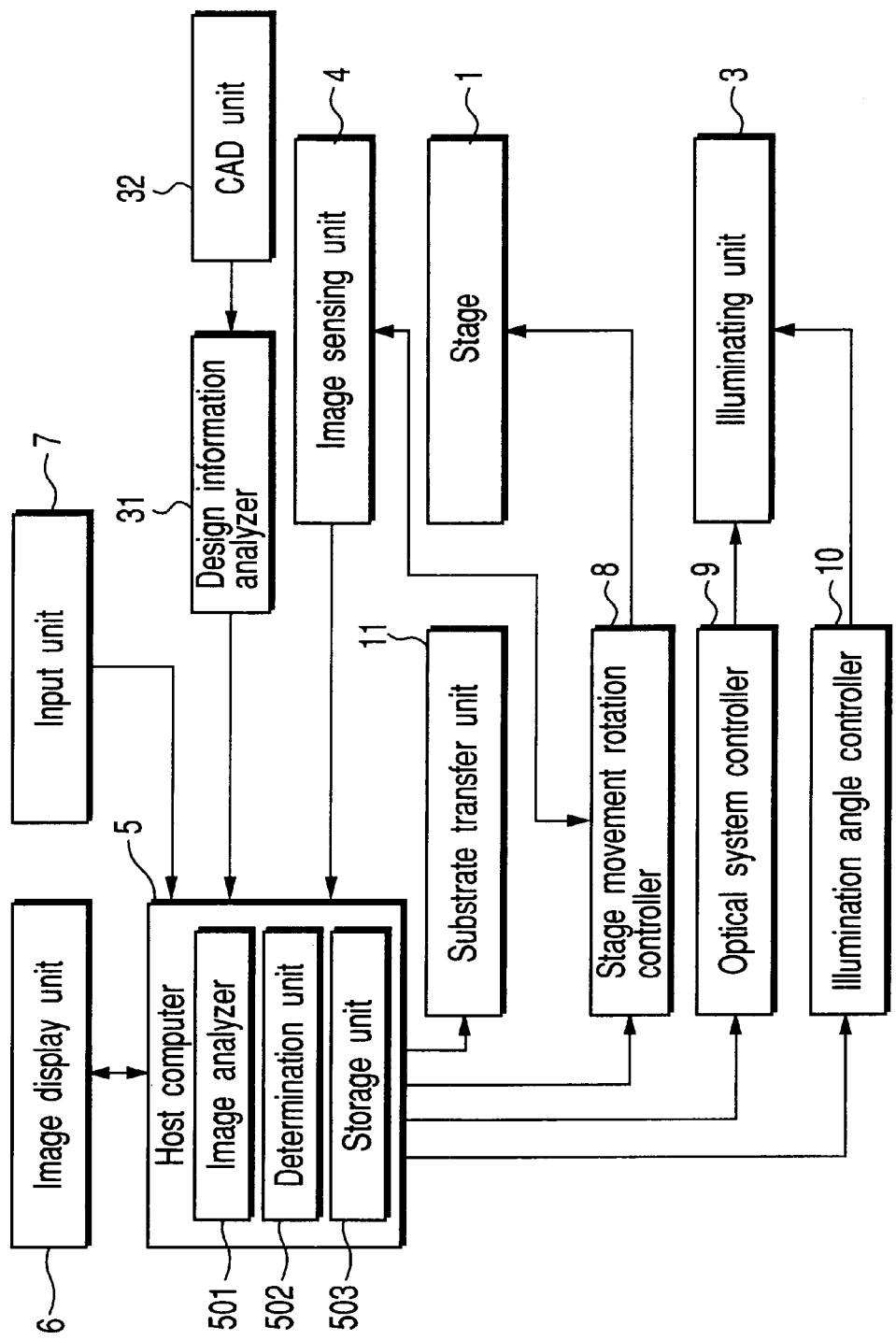
FIG. 2 is a view showing an outline of the configuration of a control system of the defect detecting apparatus according to the first embodiment of the present invention.

FIG. 2 is a view showing an outline of the configuration of a control system of the above defect detecting apparatus. Referring to FIG. 2, a host computer 5 is connected to the image sensing unit 4, an image display unit 6, an input unit 7, a stage movement rotation controller 8, an optical system controller 9, an illumination angle controller 10, a substrate transfer unit 11, and a design information analyzer 31. The illuminating unit 3 is connected to the optical system controller 9 and the illumination angle controller 10. The stage 1 and the image sensing unit 4 are connected to the stage movement rotation controller 8. A CAD controller 32 is connected to the design information analyzer 31.

Figure 4:
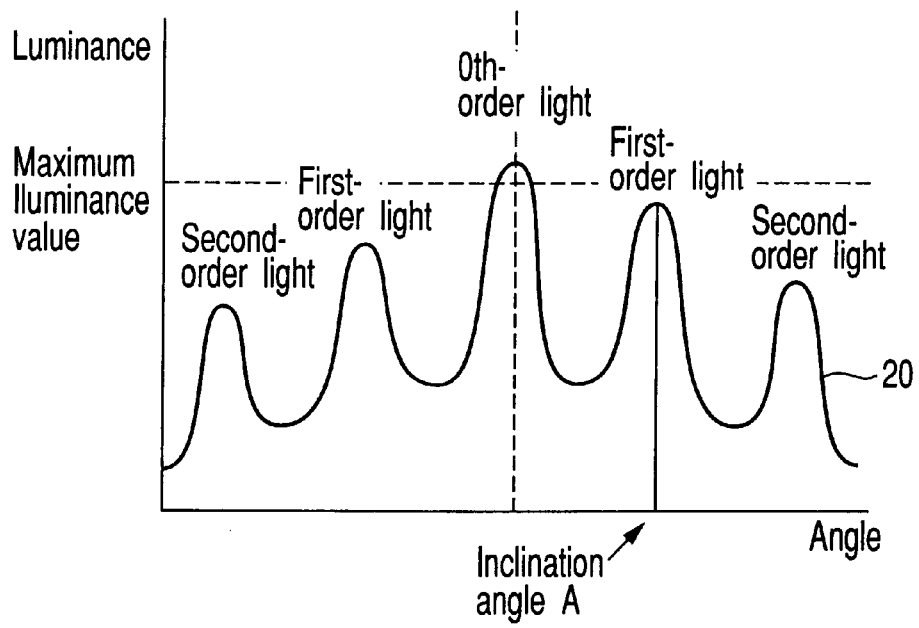
FIG. 4 is a graph showing the relationship between the luminance value and the angle according to the first embodiment of the present invention.

The host computer 5 has an image analyzer 501, a determination unit 502, and a storage unit 503. This host computer 5 has a function of executing various control operations necessary to set that inclination angle of the illuminating unit 3, which is best suited to sensing an image of the diffracted light. The image analyzer 501 receives information from the host computer 5, and generates a graph showing the relationship between the luminance value and the angle as shown in FIG. 4 (to be described later). The image analyzer 501 analyzes an image sensed by the image sensing unit 4, extracts defects such as film thickness variations, dust, and flaws on the semiconductor wafer 2, and causes the image display unit 6 to display information such as the types, numbers, positions, and areas of these defects. On the basis of this graph generated by the image analyzer 501 and showing the relationship between the luminance value and the angle, the determination unit 502 determines the position of the nth-order light, which is best suited to observation, of the diffracted light sensed by the image sensing unit 4.

The stage movement rotation controller 8 moves the stage 1 having the semiconductor wafer 2 placed on it in one direction at a pitch synchronizing with image sensing by the image sensing unit 4, and also controls rotation and positioning of the stage 1. The semiconductor wafer 2 can be rotated by rotating the stage 1 itself. However, it is favorable to form a rotary stage for placing a semiconductor wafer on it on the uniaxially movable stage 1 and rotate this rotary stage. To acquire an interference image, the optical system controller 9 controls the insertion of an interference filter 41 and the light amount of the illuminating unit 3. The illumination angle controller 10 controls the inclination angle of the illuminating unit 3 with respect to the surface of the semiconductor wafer 2 in accordance with instructions from the host computer 5. The substrate transfer unit 11 picks up semiconductor wafers 2 one by one from a storage stocker (cassette, not shown) and places the semiconductor wafer 2 on the stage 1. After defect inspection, the substrate transfer unit 11 returns the semiconductor wafer 2 on the stage 1 to the stocker.

The operation of the defect detecting apparatus configured as above will be described below.

Figure 3:
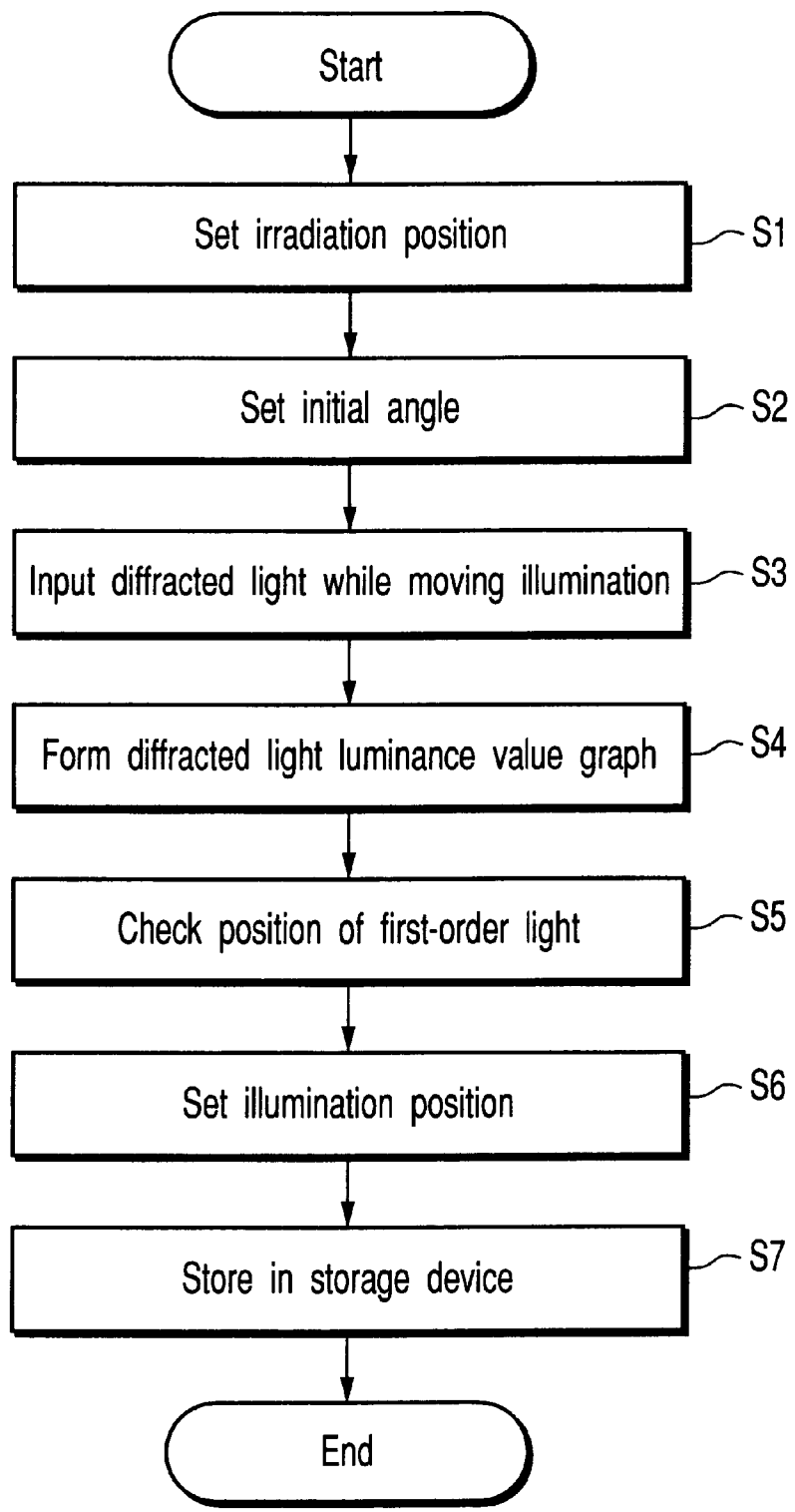
FIG. 3 is a flow chart showing the procedure of setting the inclination angle of an illuminating unit in the defect detecting apparatus according to the first embodiment of the present invention.

FIG. 3 is a flow chart showing the procedure of setting the inclination angle of the illuminating unit in the above defect detecting apparatus. First, that inclination angle of the illuminating unit 3, which is best suited to sensing an image of the diffracted light is set. The flow chart shown in FIG. 3 is executed when an inspector designates from the input unit 7 the start of setting of an illumination angle for sensing an image of the diffracted light.

First, the substrate transfer unit 11 picks up a semiconductor wafer 2 for setting the angle of the diffracted light from the stocker (not shown), and transfers and places the semiconductor wafer 2 onto the stage 1. The stage movement rotation controller 8 positions this stage 1 on which the semiconductor wafer 2 is placed.

In step S1, the host computer 5 sets on the semiconductor wafer 2 a position which the illuminating unit 3 irradiates with linear illuminating light. In step S2, the illumination angle controller 10 sets the inclination angle of the illuminating unit 3 with respect to the surface of the semiconductor wafer 2 to an initially set angle (rotation start position). In step S3, while the inclination angle of the illuminating unit 3 is changed in turn from this initially set angle, the image sensing unit 4 receives the diffracted light from the surface of the semiconductor wafer 2 at each inclination angle. The data of the diffracted light thus received by the image sensing unit 4 is supplied to the host computer 5.

In step S4, the host computer 5 calculates the average value of the luminance values of the diffracted light received by the image sensing unit 4 at each inclination angle of the illuminating unit 3, and outputs to the image analyzer 501 these average luminance values as luminance values corresponding to the individual inclination angles. The image analyzer 501 performs image processing to generate a graph 20, as shown in FIG. 4, which indicates the relationship between the luminance value and the angle. The image analyzer 501 then supplies information based on the graph to the determination unit 502.

In step S5, on the basis of the above graph, the determination unit 502 determines the position of the nth-order light, which is best suited to observation, of the diffracted light sensed by the image sensing unit 4. The determination result obtained by the determination unit 502 is supplied to the illumination angle controller 10. In step S6, the illumination angle controller 10 sets that angle (A shown in FIG. 4) on the graph, which corresponds to the position of, e.g., the first-order light determined to be best suited to observation by the determination unit 502, as an inclination angle A of the illuminating unit 3 with respect to the semiconductor wafer 2. In step S7, the set inclination angle A is stored in the storage unit 503 of the host computer 5.

The setting of the inclination angle of the illuminating unit 3 as described above is performed for each type of object to be inspected and for each fabrication step of the object. Each individual set inclination angle is stored in the storage unit 503. When defect inspection is performed for the same type of object in the same step, the inclination angle stored in the storage unit 503 is used.

Next, defects of a semiconductor wafer 2 are inspected with the illuminating unit 3 thus set at the optimum inclination angle A. First, the inspector designates the start of defect inspection from the input unit 7. The substrate transfer unit 11 picks up a semiconductor wafer 2 as an object to be inspected from the stocker (not shown), and transfers and places the semiconductor wafer 2 onto the stage 1. From this state, the stage movement rotation controller 8 moves the stage 1 in one direction (X direction) at a constant velocity. In synchronism with this movement, the image sensing unit 4 senses an image of the diffracted light line by line in a direction perpendicular to the moving direction of the stage 1. Each diffracted image sensed by the image sensing unit 4 is transferred to the image analyzer 501 until the entire surface of the semiconductor wafer 2 is completely scanned.

When diffracted images from the entire surface of the semiconductor wafer 2 are completely sensed after that, the optical system controller 9 inserts the interference filter 41 into the image sensing optical path, and optimally controls the light amount of the illuminating unit 3. Also, the illumination angle controller 10 sets the inclination angle of the illuminating unit 3 with respect to the surface of the semiconductor wafer 2 to an optimum angle for sensing an interference image. The setting of the optimum angles of the illuminating unit 3 and the image sensing unit 4 with respect to an interference image is done by a method of any of the 18th to 21st embodiments to be described later.

From this state, the stage movement rotation controller 8 moves the stage 1 at a constant velocity in a direction opposite to the diffracted image sensing direction. In synchronism with this movement, the image sensing unit 4 senses an image of the interference light line by line in the direction perpendicular to the moving direction of the stage 1. Each interference image sensed by the image sensing unit 4 is transferred to the image analyzer 501 until the entire surface of the semiconductor wafer 2 is completely scanned.

When the diffracted images and interference images from the whole surface of the semiconductor wafer 2 are completely sensed after that, the image analyzer 501 analyzes these images. By this processing, defects such as film thickness variations, dust, and flaws on the semiconductor wafer 2 are extracted, and pieces of information such as the types, numbers, positions, and areas of these defects are displayed on the image display unit 6. The image analyzer 501 can also classify these pieces of information on the extracted defects in accordance with their types or the like, and store the classified information in the storage unit 503. It is also possible to display the sensed diffracted images and interference images on the image display unit 6, and allow the inspector to visually check these images to extract defects.

The semiconductor wafer 2 thus completely inspected is returned to the stocker by the substrate transfer unit 11. Subsequently, the substrate transfer unit 11 transfers an uninspected semiconductor wafer 2 from the stocker and places it on the stage 1. Before diffracted images are re-sensed, the inclination angle A of the illuminating unit 3 stored in the storage unit 503 of the host computer 5 is read out. The illumination angle controller 10 automatically sets the inclination angle of the illuminating unit 3 with respect to the semiconductor wafer 2 to the optimum state, i.e., the angle A.

In this first embodiment, while the inclination angle of the illuminating unit 3 is changed, the diffracted light from the surface of the semiconductor wafer 2 is received by the image sensing unit 4 at each inclination angle. The average value of the luminance values of the diffracted light is calculated, and the graph 20, as shown in FIG. 4, which indicates the relationship between the average luminance value and the inclination angle is generated. The first-order light of the diffracted light is determined from this graph, and the inclination angle of the illuminating unit 3 is set on the basis of this determination result. Consequently, it is possible to automatically set that inclination angle of the illuminating unit 3, which is best suited to sensing an image of the diffracted light, to easily obtain high-quality diffracted images, and to perform accurate defect detection on the basis of these diffracted images. Additionally, the inclination angle of the illuminating unit 3 is set beforehand for a semiconductor wafer 2 for angle setting, and applied to defect inspection of semiconductor wafers 2 after that. Accordingly, semiconductor wafers 2 having diverse patterns can be inspected.

Outlines of the configuration of an image sensing system, an illuminating system and a control system of a defect detecting apparatus according to the second embodiment of the present invention are similar to those shown in FIGS. 1 and 2, respectively. In this second embodiment, two or more illuminating light irradiation positions are set on a semiconductor wafer 2. As in the first embodiment, a substrate transfer unit 11 picks up a semiconductor wafer 2 for setting the angle of diffracted light from a stocker (not shown), and places the semiconductor wafer 2 on a stage 1. Next, a host computer 5 sets those irradiation positions on the semiconductor wafer 2, which an illuminating unit 3 irradiates with linear illuminating light.

Figure 5:
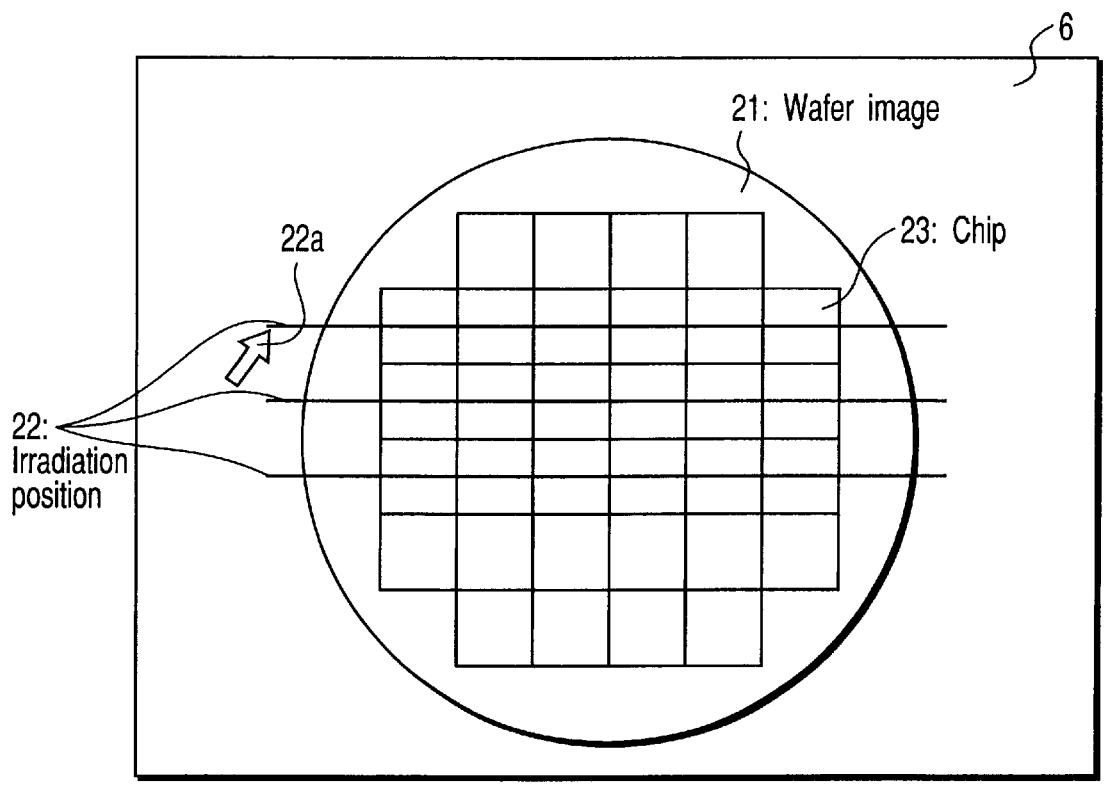
FIG. 5 is a view showing a display example of an image display unit in a defect detecting apparatus according to the second embodiment of the present invention.

FIG. 5 is a view showing a display example on an image display unit 6 in the defect detecting apparatus according to the second embodiment of the present invention. In this second embodiment, an image of the surface of the semiconductor wafer 2 is sensed in advance, and a wafer image 21 is displayed on the image display unit 6 as shown in FIG. 5. An inspector moves a cursor 22a displayed on the image display unit 6 from an input unit 7, and sets two or more linear illuminating light irradiation positions 22 on the displayed wafer image 21.

To set these irradiation positions 22, the vertical size (the size in the moving direction of the stage 1) of a chip 23 on the wafer image 21 is input beforehand. A first irradiation position 22 is set on a predetermined chip 23 by the cursor 22a. In addition, second and subsequent irradiation positions 22 shifted by the size of one chip 23 from this irradiation position 22 on the first chip 23 are automatically set in turn in the row direction on the wafer image 21. These irradiation positions 22 are in the same position on the individual chips 23. It is of course also possible to individually set these irradiation positions 22 by the cursor 22a. Furthermore, it is possible to set a line (vertical cursor) perpendicular to the line (horizontal cursor) of each irradiation position 22, and set irradiation positions by thus narrowing the setting region.

In this state, an illumination angle controller 10 sets the inclination angle of the illuminating unit 3 with respect to the surface of the semiconductor wafer 2 to an initially set angle as the rotation start position. While the inclination angle of the illuminating unit 3 is changed in turn from the initially set angle with respect to the first irradiation position 22 on the semiconductor wafer 2, an image sensing unit 4 receives the diffracted light from the surface of the semiconductor wafer 2 at each inclination angle. The data of the diffracted light thus received by the image sensing unit 4 is supplied to the host computer 5.

The host computer 5 calculates the average value of the luminance values of the diffracted light received at each inclination angle of the illuminating unit 3, and outputs to an image analyzer 501 these average luminance values as luminance values corresponding to the individual inclination angles. The image analyzer 501 performs image processing to generate a graph 20, as shown in FIG. 4, which indicates the relationship between the luminance value and the angle. The operation of calculating the average value of the luminance values of the diffracted light and the generation of the graph are performed for all irradiation positions 22. The image analyzer 501 generates those graphs indicating the relationship between the luminance value and the angle, which correspond to the individual irradiation positions 22, and supplies information based on these graphs to a determination unit 502.

On the basis of these graphs, the determination unit 502 calculates the average of the positions of the first-order light of the diffracted light sensed by the image sensing unit 4, and determines that this average value is the position of the first-order light of the diffracted light in all irradiation positions 22. This determination result obtained by the determination unit 502 is supplied to the illumination angle controller 10. In accordance with the determination result, the illumination angle controller 10 sets the inclination angle of the illuminating unit 3 with respect to the semiconductor wafer 2. The set inclination angle is stored in a storage unit 503 of the host computer 5.

In this second embodiment, two or more linear illuminating light irradiation positions are set on the semiconductor wafer 2, and the average value of the luminance values of the diffracted light in each position is calculated. Also, the graph 20 indicative of the relationship between each average luminance value and the angle is generated. The first-order light of the diffracted light is detected from the average of these graphs, and the inclination angle of the illuminating unit 3 with respect to the semiconductor wafer 2 is set. Accordingly, the inclination angle can be set with higher accuracy than in the first embodiment described above.

In the above second embodiment, the average value of the luminance values is calculated in the generation of a graph. However, methods of statistics such as a maximum value and a standard deviation can also be used. Furthermore, the luminance value of each line can be predicted and weighted by comparing it with an interference image described earlier.

Outlines of the configuration of an image sensing system, an illuminating system and a control system of a defect detecting apparatus according to the third embodiment of the present invention are similar to those shown in FIGS. 1 and 2, respectively. In this third embodiment, even when the first-order light of the diffracted light cannot be well detected owing to the state of patterns on a semiconductor wafer 2, an illuminating unit is set at an optimum angle with which an image of the first-order light of the diffracted light can be sensed.

Figure 6:
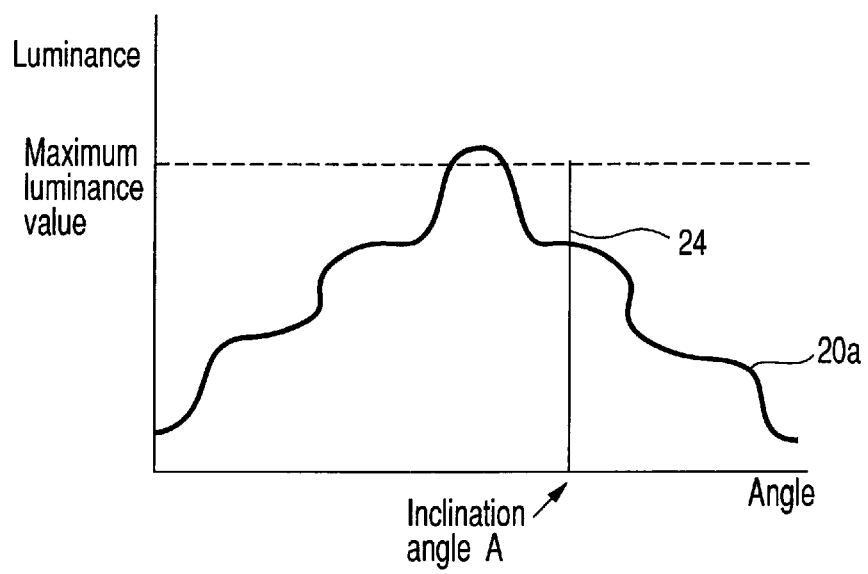
FIG. 6 is a graph showing the relationship between the luminance value and the angle according to the third embodiment of the present invention.

In the first and second embodiments, a peak at the position of the nth-order light unclearly appears, as shown in FIG. 6, depending on the state of patterns on a semiconductor wafer 2, in a graph generated by an image analyzer 501 and indicating the relationship between the angle and the average luminance value of the diffracted light received at each inclination angle of an illuminating unit 3. The first-order light position of the diffracted light cannot be detected from this graph 20a, so a determination unit 502 cannot determine the first-order light of the diffracted light. In this case, a host computer 5 sets a predetermined angle (a preset reference inclination angle) prestored in a storage unit 503 and corresponding to the first-order light position, e.g., an angle at which flaws can be easily seen in a dark field image. This predetermined angle is any of an angle previously obtained by simulation, an inclination angle used in the previous defect detection, and an angle shifted about 5° to 10° from 45° at which a dark field image can be acquired. Alternatively, an inspector can designate a position 24 assumed to be the first-order light of the diffracted light on the graph 20a shown in FIG. 6. On the basis of the set angle or the designated position 24 of the first-order light of the diffracted light, an illumination angle controller 10 sets the inclination angle of the illuminating unit 3 with respect to the semiconductor wafer 2. This inclination angle is stored in the storage unit 503 of the host computer 5.

Furthermore, for each of a plurality of (e.g., five) semiconductor wafers 2 in a stocker (not shown), the image analyzer 501 can generate a graph 20, as shown in FIG. 4, which indicates the relationship between the luminance value and the angle. In this case, an inspector designates the position of the first-order light of the diffracted light on the most appropriate graph selected from an input unit 7. Alternatively, the determination unit 502 can select the most appropriate one of the graphs generated by the image analyzer 501, and automatically sets the position of the first-order light of the diffracted light on that graph. In any case, even when the first-order light of the diffracted light as shown in FIG. 6 cannot be detected in any of a plurality of graphs, the position of the first-order light of the diffracted light can be determined from the most appropriate graph as shown in FIG. 4. The determination unit 502 can also calculate the average value of the positions of the first-order light of the diffracted light from the plurality of graphs, or calculate the position of the first-order light of the diffracted light at which the luminance value is a maximum, and automatically set that position. In the above processing for a plurality of semiconductor wafers 2, a semiconductor wafer 2 whose graph is largely different from those of other semiconductor wafers 2 is excluded from objects of inspection.

In this third embodiment, when the first-order light of the diffracted light cannot be well detected owing to the state of patterns on the semiconductor wafer 2, a predetermined reference angle is set, or the position 24 of the first-order light of the diffracted light is designated on a graph. Furthermore, the most appropriate graph is chosen from a plurality of graphs 20 generated for a plurality of objects (semiconductor wafers) to be inspected, or the position of the first-order light is calculated from the average value of a plurality of graphs. Consequently, even when an inappropriate graph as shown in FIG. 6 is generated, it is possible to set an optimum angle of the illuminating unit 3 at which an image of the first-order light of the diffracted light can be accurately sensed.

Outlines of the configuration of an image sensing system, an illuminating system and a control system of a defect detecting apparatus according to the fourth embodiment of the present invention are similar to those shown in FIGS. 1 and 2, respectively. In this fourth embodiment, the irradiation positions of an illuminating unit are set for a plurality of subdivided regions differing in, e.g., pattern width, shape, and direction in one chip on a semiconductor wafer 2. As in the first to third embodiments, a substrate transfer unit 11 picks up a semiconductor wafer 2 for setting the angle of diffracted light from a stocker (not shown), and places the semiconductor wafer 2 on a stage 1. Next, a host computer 5 sets on the semiconductor wafer 2 the position of an illuminating unit 3 which irradiates illuminating light.

Figure 7:
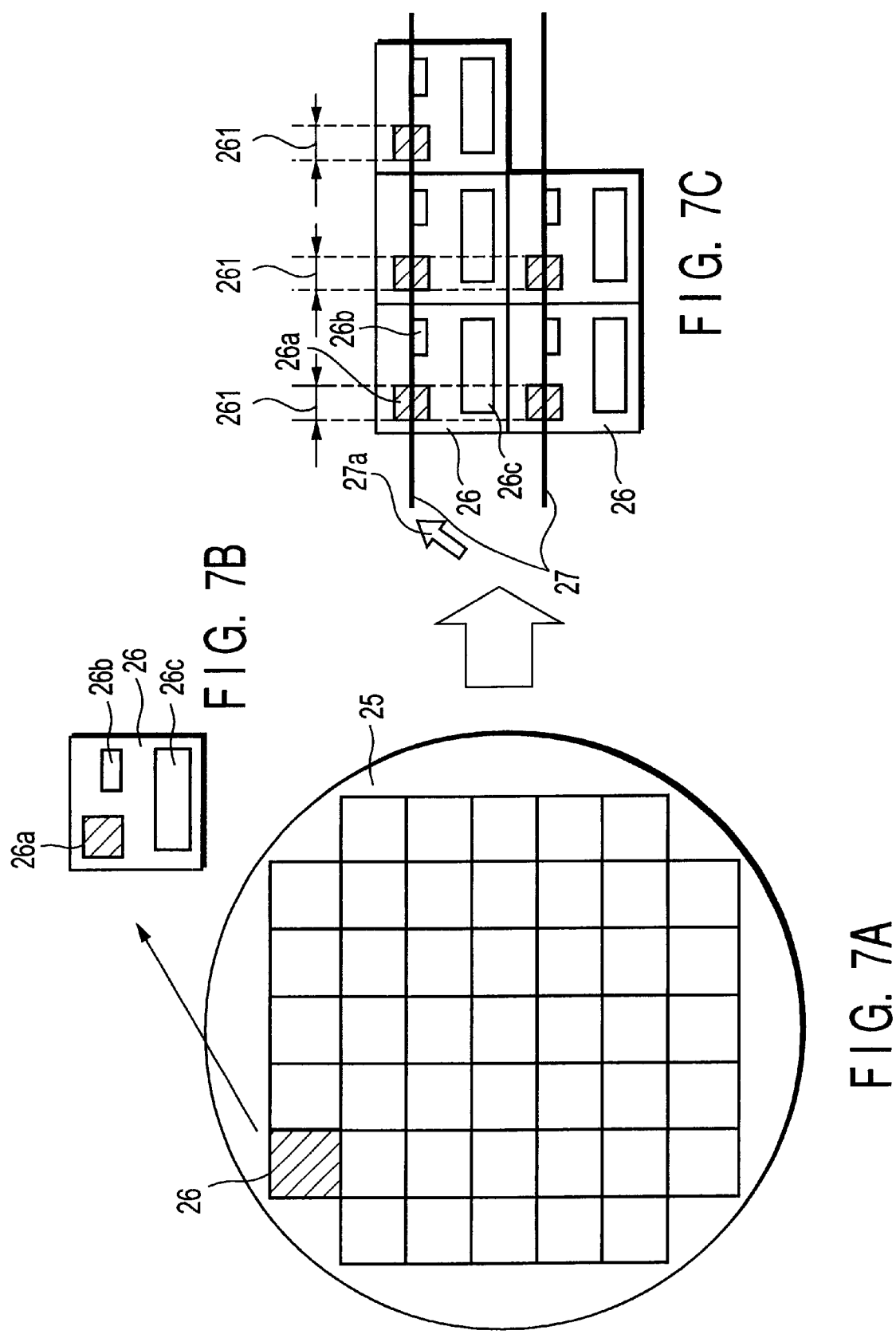
FIGS. 7A, 7B, and 7C are views showing a display example of an image display unit in a defect detecting apparatus according to the fourth embodiment of the present invention.

FIG. 7A is a view showing a display example on an image display unit 6 in the defect detecting apparatus according to the fourth embodiment of the present invention. FIGS. 7B and 7C are partial enlarged views of FIG. 7A. In this embodiment, an image of the surface of the semiconductor wafer 2 is sensed beforehand, and a wafer image 25 is displayed on the image display unit 6 as shown in FIG. 7A. A large number of chips 26 arranged in a matrix manner are displayed in the wafer image 25. As shown in FIG. 7B, each chip 26 has a plurality of pattern regions 26a, 26b, and 26c different in, e.g., pattern width, shape, and direction.

In this state, an inspector operates an input unit 7 to move a cursor 27a displayed on the image display unit 6, thereby designating the column of a predetermined chip 26 on the wafer image 25 and also designating a predetermined region. If the inspector designates a region 261 corresponding to the pattern region 26a by a mouse pointer or the like on the cursor 27a which designates the pattern region 26a, the host computer 5 sets an illuminating light irradiation position 27 on the wafer image 25 such that, as shown in FIG. 7C, this irradiation position 27 crosses the region 261 corresponding to the pattern region 26a of each chip 26. If chips 26 are also present in the row direction, the size (vertical size) of one chip 26 from the irradiation position 27 is calculated, and another irradiation position 27 is so set as to cross a region 261 corresponding to a pattern region 26a of each chip 26.

In this state, an illumination angle controller 10 sets the inclination angle of the illuminating unit 3 with respect to the surface of the semiconductor wafer 2 to an initially set angle as the rotation start position. From this state, while the inclination angle of the illuminating unit 3 is changed in turn with respect to the first irradiation position 27 on the semiconductor wafer 2, an image sensing unit 4 receives the diffracted light from the surface of the pattern 26a corresponding to the region 261 at each inclination angle. The data of the diffracted light thus received by the image sensing unit 4 is supplied to the host computer 5.

The host computer 5 calculates the average value of the luminance values of the diffracted light corresponding to the region 261 received at each inclination angle of the illuminating unit 3, and outputs to an image analyzer 501 these average luminance values as luminance values corresponding to the individual inclination angles. The image analyzer 501 performs image processing to generate a graph 20, as shown in FIG. 4, which indicates the relationship between the luminance value and the angle. The operation of calculating the average value of the luminance values of the diffracted light and the generation of the graph are performed for a plurality of irradiation positions 27. The image analyzer 501 generates those graphs indicating the relationship between the luminance value and the angle, which correspond to the individual irradiation positions 27, and supplies information based on these graphs to a determination unit 502.

On the basis of these graphs, the determination unit 502 calculates the average of the positions of the first-order light of the diffracted light with respect to each pattern region 26a, and determines that this average value is the position of the first-order light of the diffracted light in all irradiation positions 27. This determination result obtained by the determination unit 502 is supplied to the illumination angle controller 10. In accordance with the determination result, the illumination angle controller 10 sets the inclination angle of the illuminating unit 3 with respect to the semiconductor wafer 2. The set inclination angle is stored in a storage unit 503 of the host computer 5.

In this fourth embodiment, the pattern region 26a of the chip 26 is described. However, the first-order light of the optimum diffracted light can be detected for the other pattern regions 26b and 26c by similarly setting regions and irradiation positions in these pattern regions 26b and 26c. Consequently, an image of the first-order light of the diffracted light can be sensed while optimum irradiation positions are individually set for the pattern regions 26a, 26b, and 26c of the chip 26. It is also possible to set a plurality of irradiation positions within the range of one pattern 26a (patterns 26a of one column), calculate the average of the positions of the first-order light of the diffracted light in these irradiation positions, and determine that this average value is the position of the first-order light of the diffracted light in all irradiation positions.

Regions corresponding to the pattern regions 26a to 26c on the chip 26 can also be set by using CAD information (design information) used in a chip designing process. This CAD information is loaded into the host computer 5 from a CAD unit 32 via a design information analyzer 31. When this is the case, it is also possible, by setting regions from the CAD information, to detect the centers of these regions 26a to 26c and their widths in the line illuminating direction, and automatically set the irradiation position 27 and the region 261.

In this fourth embodiment, the inclination angle of the illuminating unit 3 can be set for each of the pattern regions 26a to 26c of the chip 26 on the semiconductor wafer 2. Therefore, even when detailed information of the chip 26 is desired, accurate diffracted images can be acquired.

Outlines of the configuration of an image sensing system, an illuminating system and a control system of a defect detecting apparatus according to the fifth embodiment of the present invention are similar to those shown in FIGS. 1 and 2, respectively. In this fifth embodiment, the first-order light of the diffracted light is detected by using one side (the + side or the − side of the axis of the angle around the axis of the luminance value) of a graph, generated by image analysis, which indicates the relationship between the luminance value and the angle. As in the first to fourth embodiments, a substrate transfer unit 11 picks up a semiconductor wafer 2 for setting the angle of diffracted light from a stocker (not shown), and places the semiconductor wafer 2 on a stage 1. Next, a host computer 5 sets on this semiconductor wafer 2 a position which an illuminating unit 3 irradiates with line illuminating light.

In this state, an illumination angle controller 10 sets the inclination angle of the illuminating unit 3 with respect to the surface of the semiconductor wafer 2 to an initially set angle as the rotation start position. From this state, while the inclination angle of the illuminating unit 3 is changed in turn, an image sensing unit 4 receives the diffracted light from the surface of the semiconductor wafer 2 at each inclination angle. The data of the diffracted light thus received by the image sensing unit 4 is supplied to the host computer 5.

Figure 8:
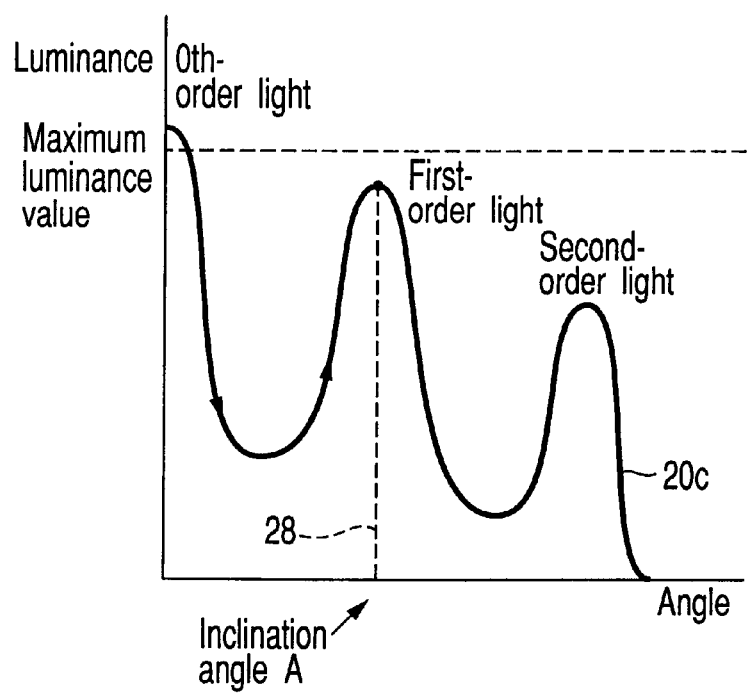
FIG. 8 is a graph showing the relationship between the luminance value and the angle according to the fifth embodiment of the present invention.

The host computer 5 calculates the average value of the luminance values of the diffracted light received by the image sensing unit 4 at each inclination angle of the illuminating unit 3, and outputs to an image analyzer 501 these average luminance values as luminance values corresponding to the individual inclination angles. The image analyzer 501 performs image processing to generate a graph 20c, as shown in FIG. 8, which indicates the relationship between the luminance value and the angle. The image analyzer 501 supplies information based on this graph to a determination unit 502.

Assuming that the 0th-order light of the diffracted light exceeding the maximum luminance value is received by the image sensing unit 4 when the inclination angle of the illuminating unit 3 is 45°, the determination unit 502 uses only the graph 20c of one side as shown in FIG. 8. That is, referring to FIG. 8, the determination unit 502 tracks the luminance value while moving to the right in FIG. 8 on the graph from the position of the 0th-order light as a peak. The determination unit 502 determines that a position 28, where the luminance value reaches the next peak after once falling from the 0th-order light position, is the position of the first-order light of the diffracted light. If a range within which the first-order light of the diffracted light exists is known to some extent, the position of the first-order light can also be determined by previously designating portions adjacent to before and after the predicted position of the first-order light as a rotating range, and detecting the peak of the graph obtained within this range. Alternatively, it is possible to designate a range within which the first-order light is reliably obtained while the inclination angle of the illuminating unit 3 is changed from the predicted position of the 0th-order light, and detect the peak of the first-order light within this range.

This determination result obtained by the determination unit 502 is supplied to the illumination angle controller 10. In accordance with the determination result, the illumination angle controller 10 sets the inclination angle of the illuminating unit 3 with respect to the semiconductor wafer 2. The set inclination angle is stored in a storage unit 503 of the host computer 5.

In this fifth embodiment, the first-order light of the diffracted light can be detected by using only the graph of one side as shown in FIG. 8, generated by image analysis, which indicates the relationship between the luminance value and the angle. Therefore, rapid angle setting can be performed. In addition, the position of the first-order light can be determined by designating the rotating range of the illuminating unit 3 as a range within which the first-order light is reliably contained. In this case, the position of the first-order light can be set more rapidly.

Outlines of the configuration of an image sensing system, an illuminating system and a control system of a defect detecting apparatus according to the sixth embodiment of the present invention are similar to those shown in FIGS. 1 and 2, respectively. In this sixth embodiment, the first-order light of the diffracted light can be detected even when the 0th-order light of the diffracted light deviates from the position of an angle of 45° as a regular reflection angle on a graph which is generated by image analysis and which indicates the relationship between the luminance value and the angle. As in the first to fifth embodiments, a substrate transfer unit 11 picks up a semiconductor wafer 2 for setting the angle of diffracted light from a stocker (not shown), and places the semiconductor wafer 2 on a stage 1. Next, a host computer 5 sets on this semiconductor wafer 2 a position which an illuminating unit 3 irradiates with line illuminating light.

In this state, an illumination angle controller 10 sets the inclination angle of the illuminating unit 3 with respect to the surface of the semiconductor wafer 2 to an initially set angle as the rotation start position. From this state, while the inclination angle of the illuminating unit 3 is changed in turn, an image sensing unit 4 receives the diffracted light from the surface of the semiconductor wafer 2 at each inclination angle. The data of the diffracted light thus received by the image sensing unit 4 is supplied to the host computer 5.

Figure 9A:
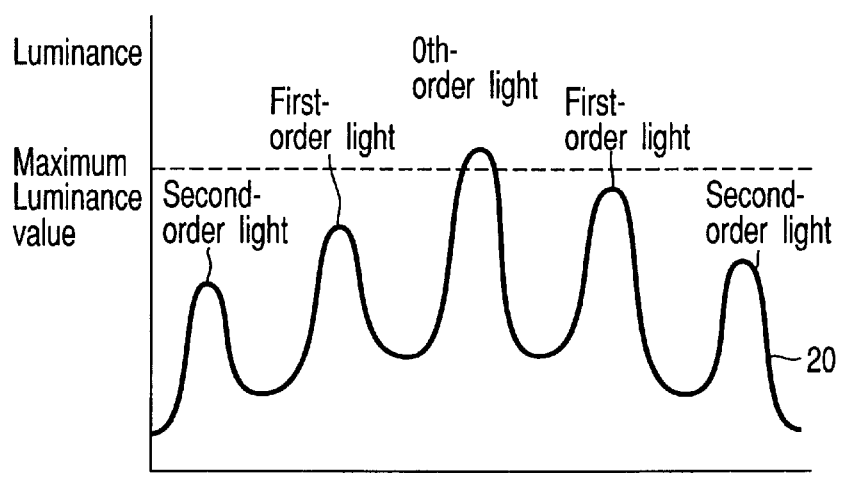
FIGS. 9A, 9B, and 9C are graphs each showing the relationship between the luminance value and the angle according to the sixth embodiment of the present invention.

The host computer 5 calculates the average value of the luminance values of the diffracted light at each inclination angle of the illuminating unit 3, and outputs to an image analyzer 501 these average luminance values as luminance values corresponding to the individual inclination angles. The image analyzer 501 performs image processing to generate a graph 20, as shown in FIG. 9A, which indicates the relationship between the luminance value and the angle. The image analyzer 501 supplies information based on this graph 20 to a determination unit 502.

Figure 9B:
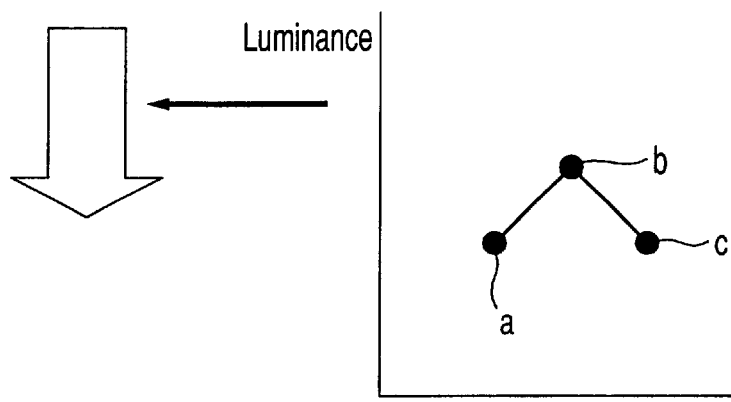
Figure 9C:
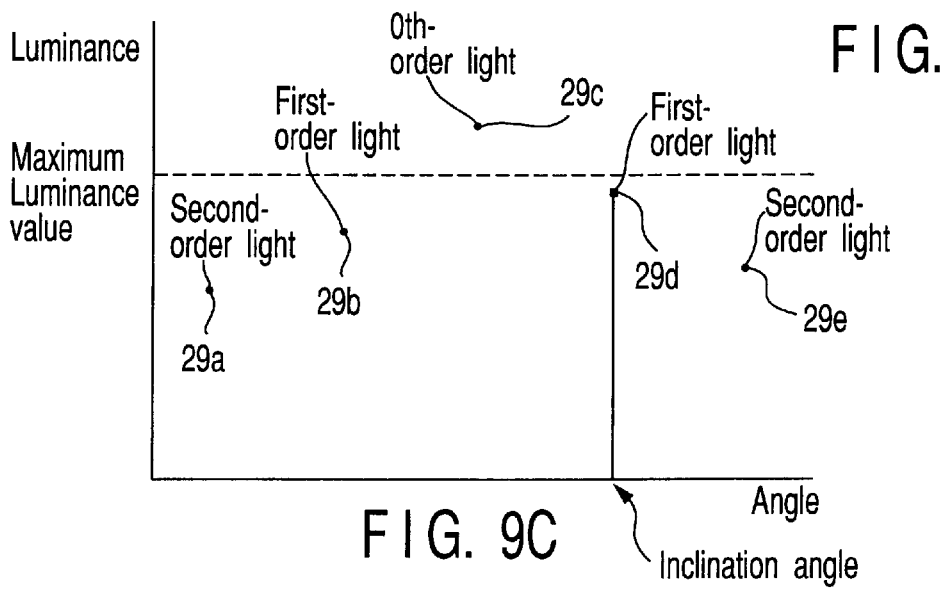

The determination unit 502 searches for each peak of the luminance value from this graph 20. On the basis of the data of three points having adjacent luminance values a, b, and c including a peak as shown in FIG. 9B, the determination unit 502 determines that the central point is the peak if the luminance value b of this central point is higher than the luminance values a and c of the two side points. In this way, the determination unit 502 tracks the luminance value while moving on the graph as shown in FIG. 9C, thereby searching for all peaks 29a to 29e. The determination unit 502 determines that, of these peaks 29a to 29e, a peak whose luminance value exceeds the maximum luminance value and is highest is the 0th-order light of the diffracted light, and the position of a peak whose luminance value does not exceed the maximum luminance value and is second highest (29d) is the first-order light of the diffracted light. That is, a position on the graph where the luminance value rises to reach a peak after falling from the highest peak is the first-order light of the diffracted light. An angle corresponding to the position of the first-order light of the diffracted light on the graph is the angle of diffraction. If the graph has noise, smoothing processing need only be performed.

This determination result obtained by the determination unit 502 is supplied to the illumination angle controller 10. In accordance with the determination result, the illumination angle controller 10 sets the inclination angle of the illuminating unit 3 with respect to the semiconductor wafer 2. The set inclination angle is stored in a storage unit 503 of the host computer 5.

In this sixth embodiment, only peaks are calculated on the graph generated by image analysis and indicating the relationship between the luminance value and the angle. Therefore, even when the 0th-order light of the diffracted light deviates from the position of an angle of 45° as a regular reflection angle, the position of the first-order light of the diffracted light can be reliably detected.

In each of the above embodiments, the detection of the first-order light of the diffracted light is consistently described. However, the inclination angle of the illuminating unit 3 with respect to the semiconductor wafer 2 can also be set by detecting the nth-order light (n is a natural number: n=1, 2, . . . ) such as the second-order light or the third-order light of the diffracted light. Also, although defect detection for the semiconductor wafer 2 is described in each of the above embodiments, the present invention is also applicable to a liquid crystal glass substrate. Furthermore, in each of the above embodiments, the inclination angle of the illuminating unit 3 is set while the image sensing unit 4 is fixed. However, the inclination angle of the image sensing unit 4 can also be set while the illuminating unit 3 is fixed.

As a consequence, the present invention according to the first to sixth embodiments can automatically set an optimum inclination angle of the illuminating unit when sensing an image of the diffracted light, and can process various objects to be inspected. Also, the present invention sets the inclination angle of the illuminating unit by detecting the first-order light of the diffracted light received from two or more irradiation positions. Accordingly, the inclination angle can be set with high accuracy. Furthermore, the present invention can set an optimum inclination angle of the illuminating unit for each designated region on an object to be inspected.

Figure 10:
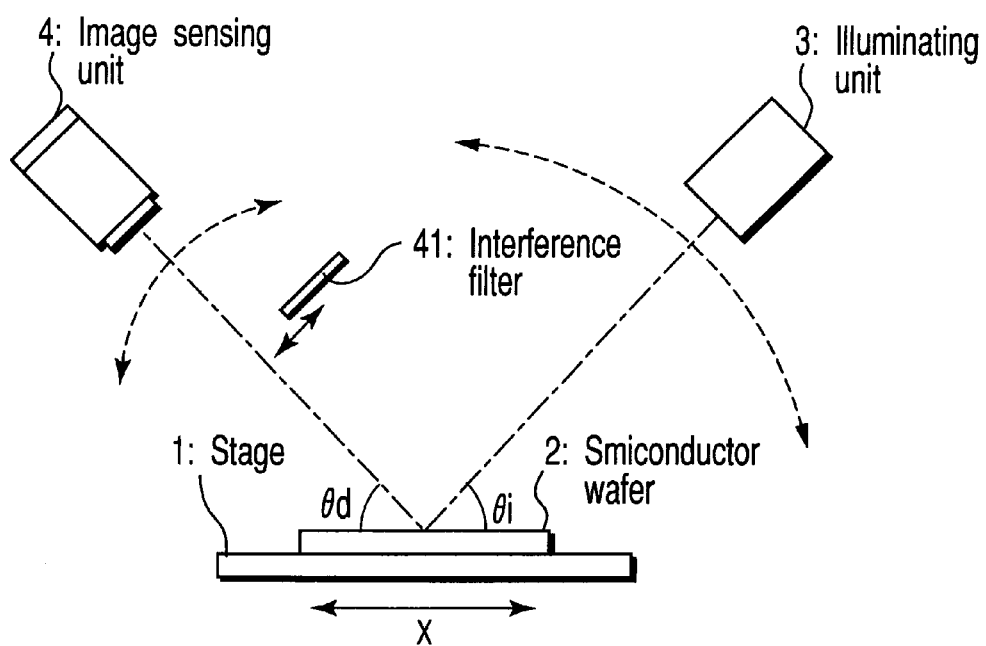
FIG. 10 is a view showing an outline of the configuration of an image sensing system and illuminating system of a defect detecting apparatus according to the seventh embodiment of the present invention.

FIG. 10 is a view showing an outline of the configuration of an image sensing system and illuminating system of a defect detecting apparatus according to the seventh embodiment of the present invention. Referring to FIG. 10, a semiconductor wafer 2 as an object to be inspected is placed on a stage 1. A linear illuminating unit 3 and an image sensing unit 4 such as a line sensor camera are arranged above the stage 1. The optical axis of the illuminating unit 3 is inclined at a predetermined angle θi to the surface of the semiconductor wafer 2. This illuminating unit 3 irradiates the surface of the semiconductor wafer 2 with linear illuminating light. The optical axis of the image sensing unit 4 is also inclined at a predetermined angle θd to the surface of the semiconductor wafer 2. This image sensing unit 4 senses line by line an image of that diffracted light from the surface of the semiconductor wafer 2, which is generated by illumination by the illuminating unit 3. Note that the optical axis of each of the image sensing unit 4 and the illuminating unit 3 is so set that the inclination angle to the surface of the semiconductor wafer 2 can be adjusted within a predetermined range.

Figure 11:
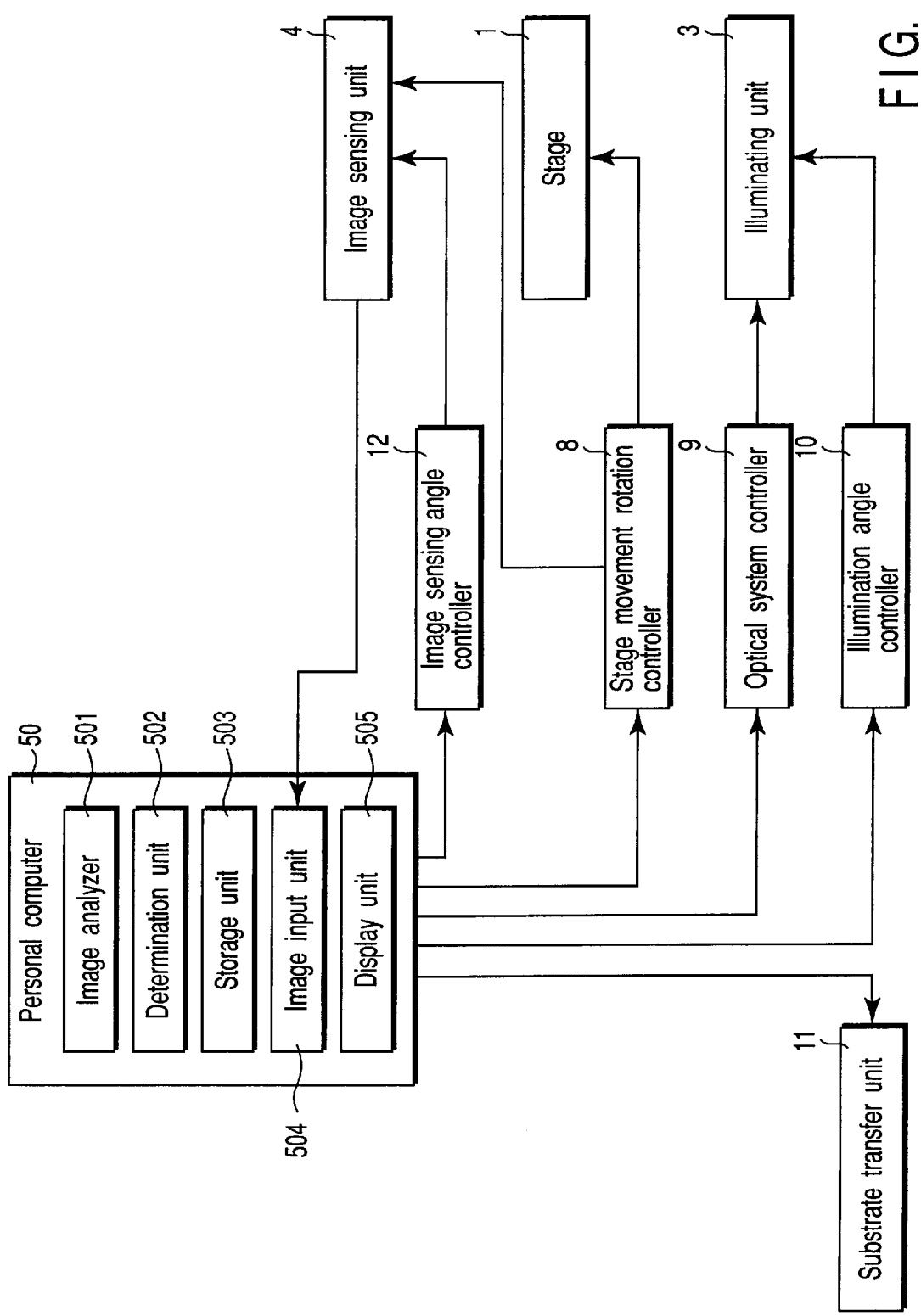
FIG. 11 is a view showing an outline of the configuration of a control system of the defect detecting apparatus according to the seventh embodiment of the present invention.

FIG. 11 is a view showing an outline of the configuration of a control system of the above defect detecting apparatus. Referring to FIG. 11, a personal computer 50 is connected to the image sensing unit 4, a stage movement rotation controller 8, an optical system controller 9, an illumination angle controller 10, a substrate transfer unit 11, and an image sensing angle controller 12. The illuminating unit 3 is connected to the optical system controller 9 and the illumination angle controller 10. The stage 1 is connected to the stage movement rotation controller 8. The image sensing unit 4 is connected to the stage movement rotation controller 8 and the image sensing angle controller 12.

The personal computer 50 has an image analyzer 501, a determination unit 502, a storage unit 503, an image input unit 504, and a display unit 505. In addition, the personal computer 5 has general functions such as a CPU, memory, hard disk, keyboard, and mouse (none of them is shown).

Figure 13:
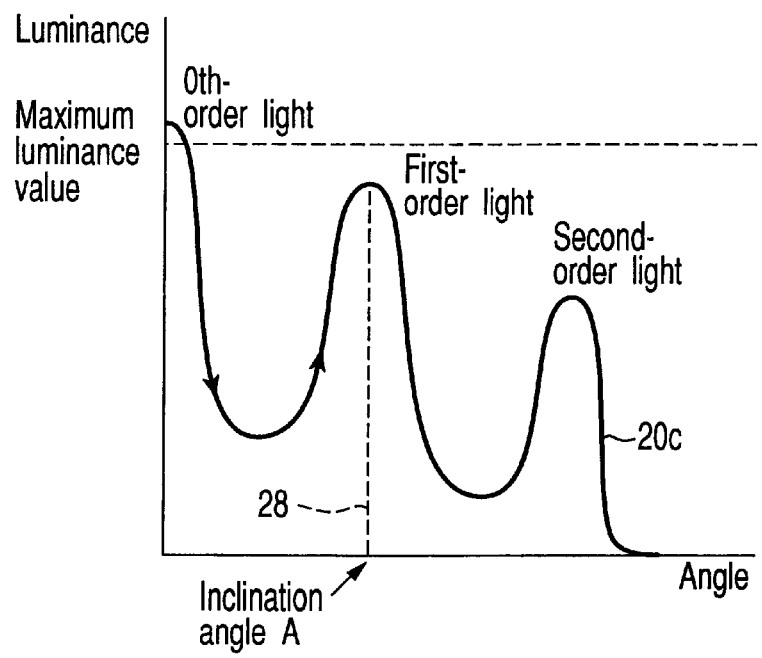
FIG. 13 is a graph showing the relationship between the luminance value and the angle according to the seventh embodiment of the present invention.

The personal computer 50 has a function of executing various control operations necessary to set those inclination angles of the illuminating unit 3 and the image sensing unit 4, which are best suited to sensing an image of the diffracted light. The image analyzer 501 generates a graph 20c, as shown in FIG. 13 (to be described later), which indicates the relationship between the luminance value and the angle. Also, the image analyzer 501 analyzes an image sensed by the image sensing unit 4, extracts defects such as film thickness variations, dust, and flaws on the semiconductor wafer 2, and causes the display unit 505 to display information such as the types, numbers, positions, and areas of these defects. On the basis of the graph generated by the image analyzer 501 and indicating the relationship between the luminance value and the angle, the determination unit 502 determines the position of the nth-order light, which is best suited to observation, of the diffracted light sensed by the image sensing unit 4.

The stage movement rotation controller 8 moves the stage 1 having the semiconductor wafer 2 placed on it in one direction at a pitch synchronizing with image sensing by the image sensing unit 4, and also controls rotation and positioning of the stage 1. To acquire an interference image, the optical system controller 9 controls the insertion of an interference filter 41 and the light amount of the illuminating unit 3. The illumination angle controller 10 controls the inclination angle of the illuminating unit 3 with respect to the surface of the semiconductor wafer 2, in accordance with instructions from the personal computer 50. The image sensing angle controller 12 controls the inclination angle of the image sensing unit 4 with respect to the surface of the semiconductor wafer 2, in accordance with instructions from the personal computer 50. The substrate transfer unit 11 picks up semiconductor wafers 2 one by one from a storage stocker (cassette, not shown) and places the semiconductor wafer 2 on the stage 1. After defect inspection, the substrate transfer unit 11 returns the semiconductor wafer 2 on the stage 1 to the stocker.

The operation of the defect detecting apparatus configured as above will be described below.

Figure 12:
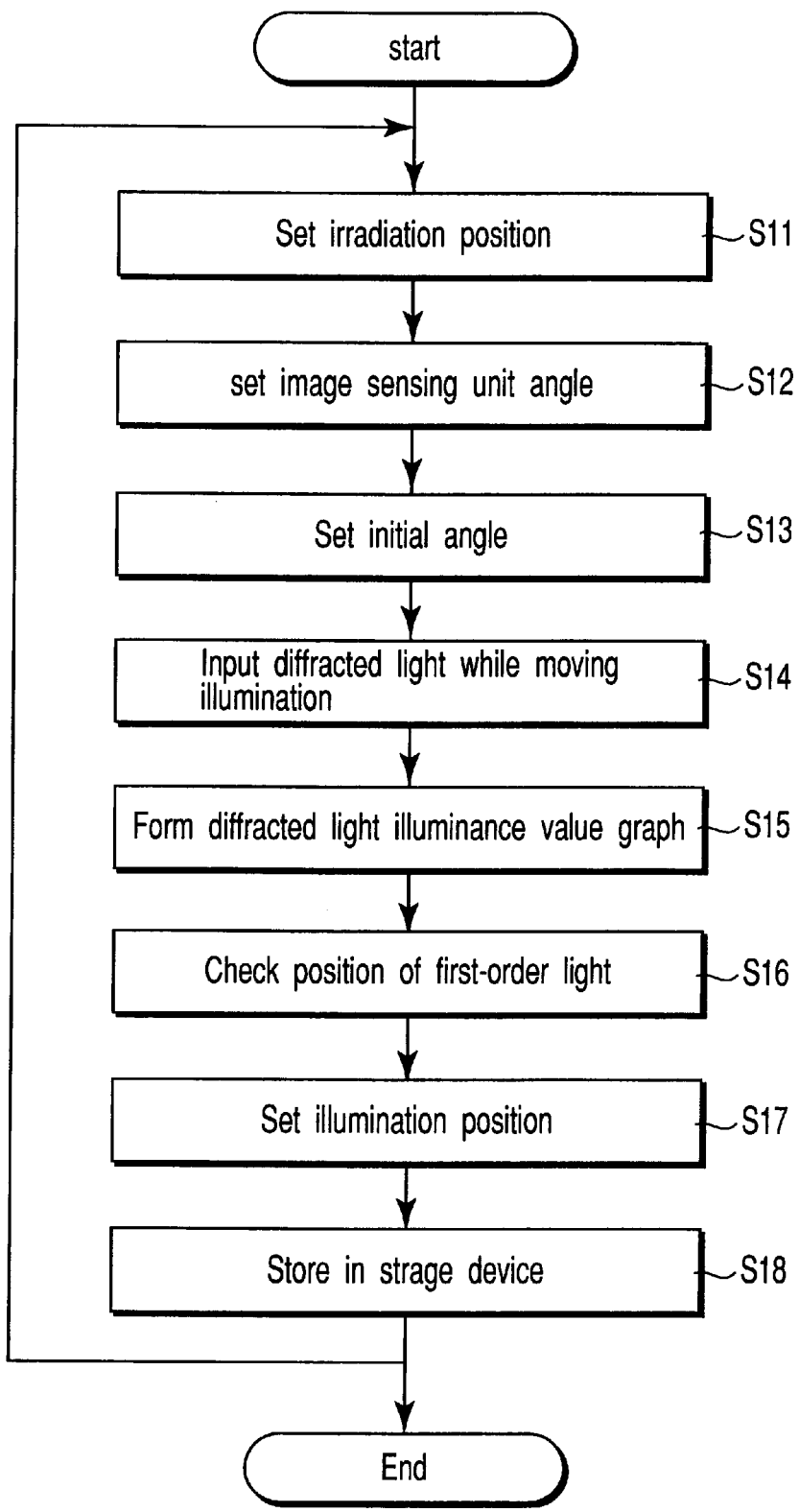
FIG. 12 is a flow chart showing the procedure of setting the inclination angles of an illuminating unit and image sensing unit in the defect detecting apparatus according to the seventh embodiment of the present invention.

FIG. 12 is a flow chart showing the procedure of setting the inclination angles of the illuminating unit and the image sensing unit in the above defect detecting apparatus. First, those inclination angles of the illuminating unit 3 and the image sensing unit 4, which are best suited to sensing an image of the diffracted light are set. The flow chart shown in FIG. 12 is executed when an inspector designates, from a menu screen (not shown) on the personal computer 50, the start of setting of an illumination angle and image sensing angle for sensing a good diffracted image.

First, the substrate transfer unit 11 picks up a semiconductor wafer 2 for setting the angle of the diffracted light from the stocker (not shown), and transfers and places the semiconductor wafer 2 onto the stage 1. The stage movement rotation controller 8 positions the stage 1 on which the semiconductor wafer 2 is placed.

In step S11, the personal computer 50 sets on the semiconductor wafer 2 a position which the illuminating unit 3 irradiates with linear illuminating light. In step S12, the image sensing angle controller 12 sets the inclination angle of the image sensing unit 4 for sensing an image of the diffracted light. In step S13, the illumination angle controller 10 sets the inclination angle of the illuminating unit 3 with respect to the surface of the semiconductor wafer 2 to an initially set angle (rotation start position). In step S14, while the inclination angle of the illuminating unit 3 is changed in turn from this initially set angle, the image sensing unit 4 receives the diffracted light line by line from the surface of the semiconductor wafer 2 at each inclination angle. The data of the diffracted light thus received by the image sensing unit 4 is supplied to the image input unit 504 of the personal computer 50.

In step S15, the image input unit 504 converts the diffracted light received by the image sensing unit 4 at each inclination angle of the illuminating unit 3 into luminance value data. The image analyzer 501 calculates the average value of the luminance values of the diffracted light received at each inclination angle of the illuminating unit 3. By using these average luminance values as luminance values corresponding to the individual inclination angles, the image analyzer 501 performs image processing to generate the graph 20c, as shown in FIG. 13, which indicates the relationship between the luminance value and the angle. The image analyzer 501 then supplies information based on this graph to the determination unit 502.

In step S16, on the basis of the above graph, the determination unit 502 determines the position of the nth-order light, which is best suited to observation, of the diffracted light sensed by the image sensing unit 4. This determination result obtained by the determination unit 502 is supplied to the illumination angle controller 10. In step S17, in accordance with the determination result from the determination unit 502, the illumination angle controller 10 sets, e.g., a first-order light inclination angle A of the illuminating unit 3 with respect to the semiconductor wafer 2. In step S18, the set inclination angle A is stored in the storage unit 503 of the personal computer 50.

If no image of the first-order light of the diffracted light is sensed by the series of operations described above, the flow returns to step S12 to change the inclination angle of the image sensing unit 4, and the diffracted light is received following the above flow chart.

Next, defects of semiconductor wafers 2 are inspected with the illuminating unit 3 and the image sensing unit thus set at the optimum inclination angle A. First, the inspector designates the start of defect inspection from the menu screen (not shown) on the personal computer 5. The substrate transfer unit 11 picks up a semiconductor wafer 2 as an object to be inspected from the stocker (not shown), and transfers and places the semiconductor wafer 2 onto the stage 1. From this state, the stage movement rotation controller 8 moves the stage 1 in one direction (X direction) at a constant velocity. In synchronism with this movement, the image sensing unit 4 senses an image of the diffracted light line by line in a direction perpendicular to the moving direction of the stage 1. Each diffracted image sensed by the image sensing unit 4 is transferred to the image analyzer 501 via the image input unit 504 until the entire surface of the semiconductor wafer 2 is completely scanned.

When diffracted images from the entire surface of the semiconductor wafer 2 are completely sensed after that, the optical system controller 9 inserts the interference filter 41 into the image sensing optical path, and optimally controls the light amount of the illuminating unit 3. Also, the illumination angle controller 10 sets the inclination angle of the illuminating unit 3 with respect to the surface of the semiconductor wafer 2 to an optimum angle for sensing an interference image. Likewise, the image sensing angle controller 6 sets the inclination angle of the image sensing unit 4 with respect to the surface of the semiconductor wafer 2 to an optimum angle for sensing an interference image. These inclination angles of the illuminating unit 3 and the image sensing unit 4 with respect to the surface of the semiconductor wafer 2 are regular reflection angles, respectively. The setting of the optimum angles of the illuminating unit 3 and the image sensing unit 4 with respect to an interference image is done by a method of any of the 18th to 21st embodiments to be described later.

From this state, the stage movement rotation controller 8 moves the stage 1 at a constant velocity in a direction (−X direction) opposite to the diffracted image sensing direction. In synchronism with this movement, the image sensing unit 4 senses an image of the interference light line by line in the direction perpendicular to the moving direction of the stage 1. Each interference image sensed by the image sensing unit 4 is transferred to the image analyzer 501 via the image input unit 504, until the entire surface of the semiconductor wafer 2 is completely scanned.

When the diffracted images and interference images from the whole surface of the semiconductor wafer 2 are completely sensed after that, the image analyzer 501 analyzes these images. By this processing, defects such as resist film thickness variations, dust, and flaws on the semiconductor wafer 2 are extracted, and pieces of information such as the types, numbers, positions, and areas of these defects are displayed on the display unit 505.

The semiconductor wafer 2 thus completely inspected is returned to the stocker by the substrate transfer unit 11. Subsequently, the substrate transfer unit 11 transfers an uninspected semiconductor wafer 2 from the stocker and places it on the stage 1. Before diffracted images are sensed, that inclination angle A of the illuminating unit 3, which is stored in the storage unit 503 of the personal computer 50 is read out. The illumination angle controller 10 automatically sets the inclination angle of the illuminating unit 3 with respect to the semiconductor wafer 2 to an optimum angle.

In this seventh embodiment, while the inclination angle of the illuminating unit 3 is changed, the diffracted light from the surface of the semiconductor wafer 2 is received by the image sensing unit 4 at each inclination angle. The average value of the luminance values of the diffracted light is calculated, and the graph 20c, as shown in FIG. 13, which indicates the relationship between the average luminance value and the inclination angle is generated. The first-order light of the diffracted light is determined from the graph, and the inclination angle of the illuminating unit 3 is set on the basis of this determination result. Consequently, it is possible to automatically set that inclination angle of the illuminating unit 3, which is best suited to sensing an image of the diffracted light, to easily obtain high-quality diffracted images, and to perform accurate defect detection on the basis of these diffracted images.

Additionally, the inclination angle of the illuminating unit 3 is set beforehand for a semiconductor wafer 2 for angle setting, not for all semiconductor wafers 2, and is applied to defect inspection of semiconductor wafers 2 after that. This can shorten the inspection time. As described above, the inclination angles of the illuminating unit 3 and the image sensing unit 4 are set by using a semiconductor wafer 2 for which defect inspection is actually performed. Accordingly, semiconductor wafers 2 having diverse patterns can be inspected.

Also, the above defect detecting apparatus uses a pair of the illuminating unit 3 and the image sensing unit 4, and can sense both a diffracted image and an interference image by changing the inclination angles of these units. More specifically, while the stage 1 on which a semiconductor wafer 2 is placed is moved forward and backward at one time, diffracted images are sensed during the forward movement, and interference images are sensed during the backward movement. In this manner, diffracted images and interference images can be obtained within a short time period. During the image sensing, the inclination angles of the illuminating unit 3 and the image sensing unit 4 are so set as to sense an image of the diffracted light during the forward movement and to sense an image of the interference light during the backward movement. Also, since the irradiation direction of the illuminating unit 3 is fixed while the stage 1 is moved back and forth, the coordinates of the sensed diffracted image and interference image can be accurately matched. To sense an image of light (e.g., scattered light) other than the diffracted light and interference light, the inclination angles of the illuminating unit 3 and the image sensing unit 4 are properly changed, and the stage 1 is moved back and forth a necessary number of times.

Figure 14:
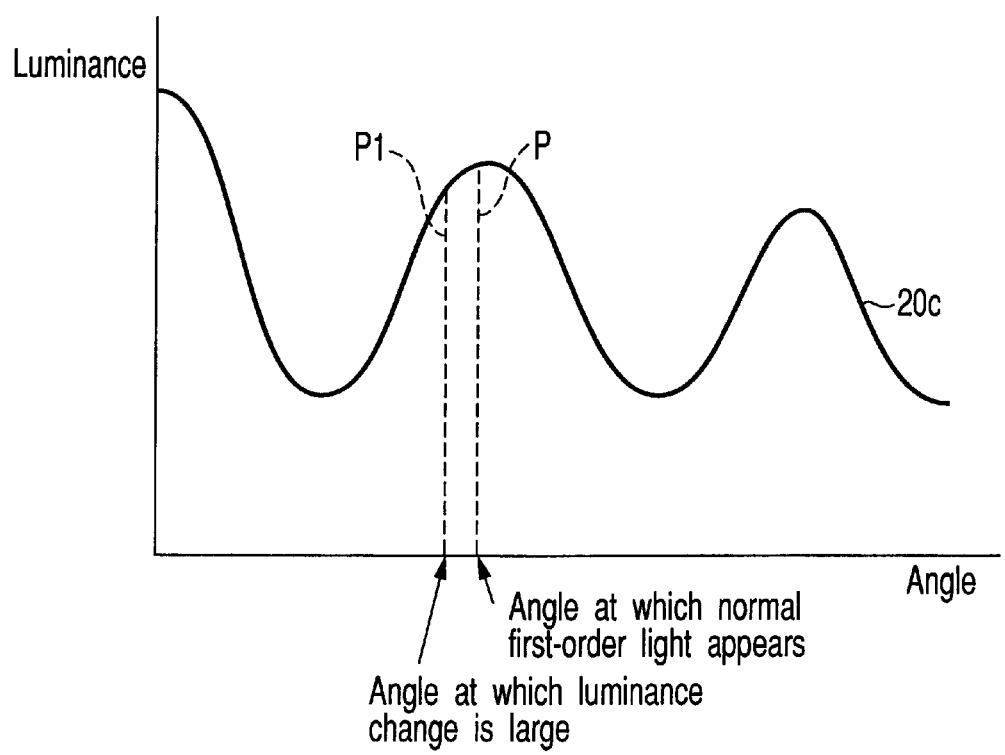
FIG. 14 is a graph showing the relationship between the luminance value and the angle according to the eighth embodiment of the present invention.

Outlines of the configuration of an image sensing system, an illuminating system and a control system of a defect detecting apparatus according to the eighth embodiment of the present invention are similar to those shown in FIGS. 10 and 11, respectively. In this eighth embodiment, as shown in FIG. 14, in a graph 20c indicating the relationship between the luminance value and the angle, an illumination angle corresponding to a luminance value peak p which corresponds to the first-order light of the diffracted light is not regarded as optimum, and an illumination angle corresponding to a portion p1 which is close to the luminance value peak p, which has a slightly smaller luminance value, and in which a change in the luminance value is large, is considered to be an optimum illumination angle. As in the seventh embodiment, a substrate transfer unit 11 picks up a semiconductor is wafer 2 from a stocker (not shown), and places the semiconductor wafer 2 on a stage 1.

Next, a graph indicative of the relationship between the luminance of the diffracted light and the illumination angle is generated in accordance with the flow chart shown in FIG. 12. To determine an optimum illumination angle, a determination unit 502 searches for a luminance value peak corresponding to the first-order light of the diffracted light on the graph. In the vicinity of a luminance value peak, the luminance value does not largely change even when the surface state of the semiconductor wafer 2 such as a pattern pitch slightly changes, so a change in the diffracted light is not sensitive. Accordingly, the determination unit 502 sets, as an optimum illumination angle, the illumination angle of a place which slightly deviates from the luminance value peak and in which a change in the luminance value is found to be large. Consequently, a diffracted image having high sensitivity to defects can be sensed.

Outlines of the configuration of an image sensing system, an illuminating system and a control system of a defect detecting apparatus according to the ninth embodiment of the present invention are similar to those shown in FIGS. 10 and 11, respectively. In this ninth embodiment, as shown in FIGS. 15A and 15B, illumination angles, pattern pitches, and image sensing angles with which the first-order to mth-order light components calculated by the following equations can be obtained are superposed and displayed on a graph 20c indicating the relationship between the luminance value of the diffracted light and the illumination angle (m is up to about the third-order light).

$$\sin \theta d - \sin \theta i = m\lambda/p \quad (1)$$

$$\theta i = \sin^{-1}(\sin \theta d - m\lambda/p) \quad (2)$$

Figure 15A:
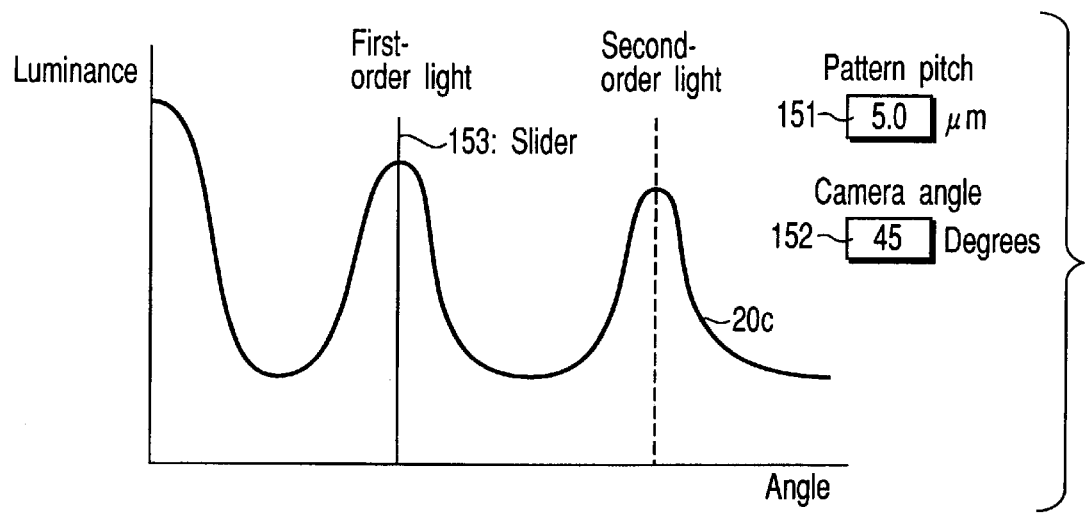
FIGS. 15A and 15B are graphs each showing the relationship between the luminance value and the illumination angle according to the ninth embodiment of the present invention.
Figure 15B:
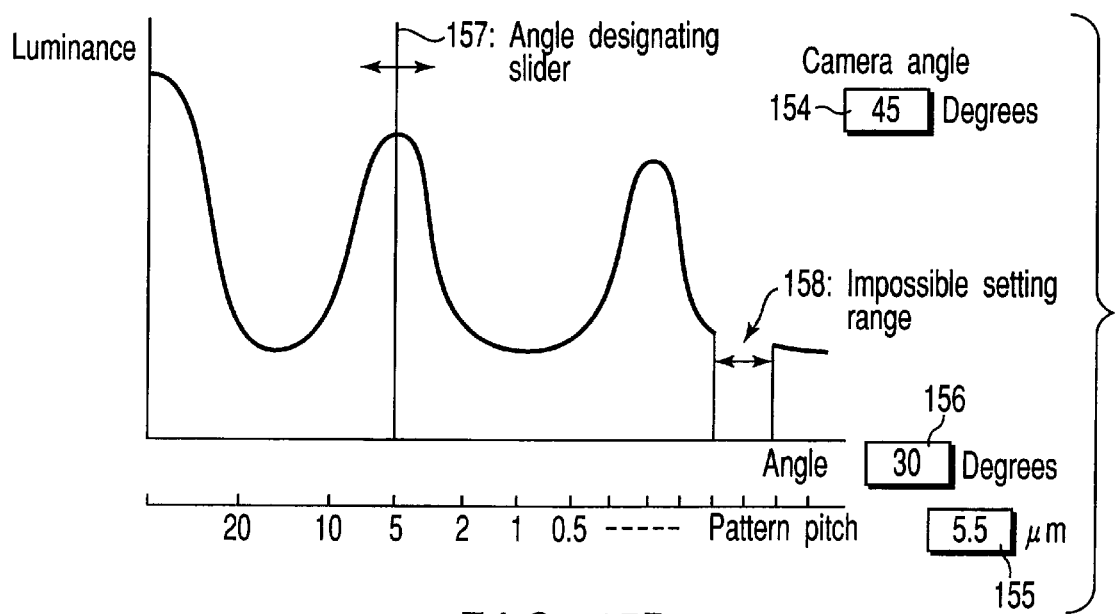

(equation (2) is obtained by expanding equation (1) by $\theta i$)
$\theta d$: the image sensing unit inclination angle
$\theta i$: the illuminating unit inclination angle
m: the order of diffracted light
$\lambda$: the wavelength of illuminating light
p: the pattern pitch Referring to FIG. 15A, a pattern pitch 151 and an image sensing angle (in FIG. 15A, a camera angle) 152 are displayed on a display unit 505 so that these values can be input, and an index, e.g., a slider 153 (or a pointer) for designating an illumination angle at which the first-order to mth-order light components appear is superposed on the graph 20c in accordance with the input values.

Referring to FIG. 15B, an image sensing angle (in FIG. 15B, a camera angle) 154 is displayed on the display unit 505 so that this value can be input, and a pattern pitch 155 and an illumination angle 156 with which the first-order light of the diffracted light appears are superposed and displayed parallel on the graph 20c. In FIG. 15B, an angle designating slider 157 for designating the inclination angle of the illuminating unit 3 is displayed. The inclination angle (illumination angle) 156 indicated by the slider 157 is displayed on the lower right corner of the graph. Accordingly, whenever an inspector moves the slider 157 to the right or left, the displayed angle is updated. By using this angle indicated by the slider 157 as an illumination angle at which the first-order light of the diffracted light appears, a pattern pitch 71 is calculated from equation (1) above, and the value is displayed on the lower right corner of the graph. In addition, when the illuminating unit 3 inclines to the image sensing unit 4, the diffracted light entering the image sensing unit 4 is sometimes interrupted depending on the inclination angle of the illuminating unit 3. In FIG. 15B, this angular range is displayed as an impossible setting range 158 of the inclination angle of the illuminating unit 3.

Furthermore, by changing the value of the pattern pitch or the image sensing angle, it is possible to immediately recalculate the illumination angle at which the first-order to mth-order light components appear or the pattern pitch at which the first-order light of the diffracted light appears, and redisplay the value on the graph. This allows the inspector to check the value of a pattern pitch which has generated the luminance peak of a graph generated from sensed diffracted light.

If no luminance peak of the first-order light exists on the graph, the inclination angle of the image sensing unit 4 is changed to perform recalculations. Consequently, the inspector can know the inclination angle of the image sensing unit 4 at which an image of the first-order light of the diffracted light can be sensed, without actually sensing an image of the diffracted light. Since this can make an actually sensed diffracted image correspond to the pattern pitch of a portion to be inspected, defect detection with higher accuracy can be performed.

Note that the graph displays are not restricted to those shown in FIGS. 15A and 15B. For example, a synthetic graph of FIGS. 15A and 15B can also be displayed.

Outlines of the configuration of an image sensing system, an illuminating system and a control system of a defect detecting apparatus according to the 10th embodiment of the present invention are similar to those shown in FIGS. 10 and 11, respectively. In this 10th embodiment, the irradiation positions of an illuminating unit are designated for a plurality of subdivided regions differing in, e.g., pattern width, shape, and direction in one chip on a semiconductor wafer 2. In addition, the contrast of the luminance value between designated regions at each irradiation position is regarded as the luminance value at the corresponding illumination angle and image sensing angle. As in the seventh to ninth embodiments, a substrate transfer unit 11 picks up a semiconductor wafer 2 from a stocker (not shown), and places the semiconductor wafer 2 on a stage 1. Next, a personal computer 50 sets on the semiconductor wafer 2 the position of an illuminating unit 3 which irradiates illuminating light.

FIG. 16A is a view showing a display example on a display unit 505 in a defect detecting apparatus according to the 11th embodiment of the present invention. FIGS. 16B and 16C are partial enlarged views of FIG. 16A. In this embodiment, an image of the surface of the semiconductor wafer 2 is sensed beforehand, and a wafer image 25 is displayed on the display unit 505 as shown in FIG. 16A. A large number of chips 26 arranged in a matrix are displayed in the wafer image 25. As shown in FIG. 16B, each chip 26 has a plurality of pattern regions 26a, 26b, and 26c different in, e.g., pattern width, shape, and direction.

In this state, an inspector designates the column of a predetermined chip 26 on the wafer image 25 and also designates a predetermined region by using a cursor 27a from a menu screen (not shown) displayed on the personal computer 50. If the inspector designates a region 261 corresponding to the pattern region 26a by a mouse pointer or the like on the cursor 27a which designates the pattern region 26a, an irradiation position 27 on the wafer image 25 is so set, as shown in FIG. 16C, as to cross the region 261 corresponding to the pattern region 26a of each chip 26. If chips 26 are also present in the row direction, the size (vertical size) of one chip 26 from the irradiation position 27 is calculated, and another irradiation position 27 is so set as to cross a region 261 corresponding to a pattern region 26a of each chip 26. Assume that the inspector designates another region 281. In each chip 26, the regions 281 is present as in the region 261.

In this state, the above defect detecting apparatus executes the operation of the flow chart shown in FIG. 12, obtaining the luminance value of the diffracted light for each of the regions 261 and 281. The contrast between the average luminance value in the region 261 and that in the region 281 is calculated and set as the luminance value of the diffracted light. A graph indicating the relationship between the luminance value of the diffracted light and the inclination angle is generated. From this graph, an illumination angle and image sensing angle at which the contrast is a maximum are obtained.

In this 11th embodiment, detailed information is obtained from a region designated by an inspector on the wafer image 25 displayed on the display unit 505. Therefore, it is possible to acquire diffracted images with higher accuracy than when a region is designated in accordance with design data.

Figure 17:
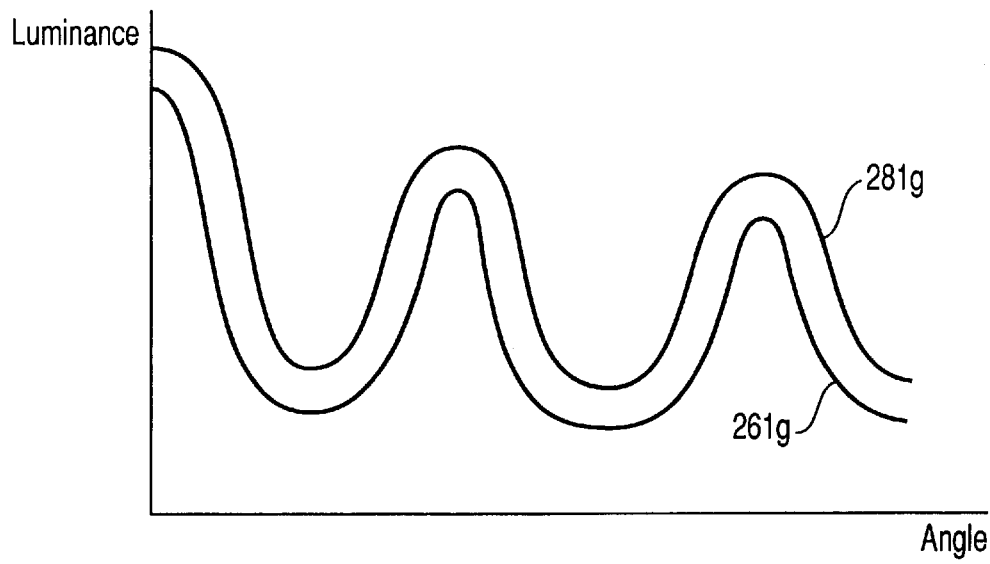
FIG. 17 is a graph showing the relationship between the luminance value and the illumination angle according to the 12th embodiment of the present invention.

Outlines of the configuration of an image sensing system, an illuminating system and a control system of a defect detecting apparatus according to the 12th embodiment of the present invention are similar to those shown in FIGS. 10 and 11, respectively. In this 12th embodiment, as shown in FIG. 17, a display unit 505 displays graphs 261g and 281g in which the luminance values of a plurality of regions, e.g., the luminance values of regions 261 and 281, respectively, shown in FIG. 16C, are related to the illumination angle. Consequently, even if the regions 261 and 281 have different pattern pitches, an optimum illumination angle corresponding to the first-order light of the diffracted light can be determined on graphs on one screen.

The graphs 261g and 281g can also be displayed in different colors on the display unit 505. This makes it possible to distinguish between these graphs 261g and 281g of the regions 261 and 281 by different colors. In this case, the average values or the maximum values of the luminance values of these regions 261 and 281 can be displayed together with the corresponding graphs 261g and 281g.

In a defect detecting apparatus according to the 13th embodiment of the present invention, the wafer image 25 described in the 11th embodiment and the graphs 261g and 281g described in the 12th embodiment are simultaneously displayed on a display unit 505. This permits an inspector to recognize the correspondence between the regions 261 and 281 on the wafer image 25 and the graphs 261g and 281g.

In a defect detecting apparatus according to the 14th embodiment of the present invention, a stage movement rotation controller 8 controls both the movement and rotation of a stage 1. The rotation of this stage 1 is controlled in accordance with the direction of the pattern on a semiconductor wafer 2 as an object to be inspected.

When the stage 1 is moved straight (X direction) while an illuminating unit 3 irradiates the surface of the semiconductor wafer 2 with linear illuminating light, an image of the diffracted light or the interference light cannot be sensed in some cases depending on the direction of the pattern on the semiconductor wafer 2. For example, an image of the diffracted light or the interference light cannot be sensed if the direction of the pattern makes an angle of 90° with respect to the line direction of the illuminating light. In a case like this, the stage movement rotation controller 8 controls the rotation of the stage 1, e.g., rotates the stage 1 90° around its central vertical line. Since this aligns the direction of the pattern on the semiconductor wafer 2 with the line direction of the illuminating line, an image of the diffracted light or the interference light can be sensed.

In this 14th embodiment, the rotation of the stage 1 is controlled in accordance with the direction of the pattern on the semiconductor wafer 2. Accordingly, an image of the diffracted light or the interference light can be sensed from patterns different in direction. Also, since the stage 1 need only be rotated a predetermined angle, the rotation operation is easier than when the illuminating unit 3 and an image sensing unit 4 are rotated together.

In a defect detecting apparatus according to the 15th embodiment of the present invention, illuminating light emitted from an illuminating unit 3 is not linear light. That is, the illuminating unit 3 illuminates the entire surface of a semiconductor wafer 2 at one time, or illuminates a portion of the surface of the semiconductor wafer 2 by spot illumination. In the former one-time illumination, plane illuminating light evenly illuminates the whole surface of the semiconductor wafer 2. Therefore, an image of the entire region of the semiconductor wafer 2 can be sensed at once. In the latter spot illumination, an image of only a desired region on the semiconductor wafer 2 can be sensed with point illuminating light.

Furthermore, by combining the above one-time illumination and the rotation control of the stage 1 described in the 14th embodiment, an image of the whole pattern on the semiconductor wafer 2 can be evenly sensed. It is also possible to sense an image of only a desired pattern in an optimum state by combining the spot illumination and the rotation control of the stage 1.

In a defect detecting apparatus according to the 16th embodiment of the present invention, an image sensing angle controller 12 three-dimensionally controls the inclination angle of an image sensing unit 4 with respect to the surface of a semiconductor wafer 2. In the eighth to 15th embodiments described above, the inclination angles of the image sensing unit 4 and the illuminating unit 3 with respect to the surface of the semiconductor wafer 2 are two-dimensionally controlled. Therefore, an image of the diffracted light or the interference light cannot always be sensed with high directivity. In this 16th embodiment, the image sensing unit 4 is three-dimensionally operated and can thereby sense an image of the diffracted light or the interference light having highest directivity in accordance with the pattern on the semiconductor wafer 2. Accordingly, it is possible to sense an image of the diffracted light or the like from a pattern which cannot be detected only by two-dimensionally controlling the inclination angle.

A similar effect can be obtained by three-dimensionally controlling the inclination angle of an illuminating unit 3 by an illumination angle controller 10, or by three-dimensionally swinging a stage 1 by a stage movement rotation controller 8, instead of three-dimensionally controlling the image sensing unit 4.

In a defect detecting apparatus according to the 17th embodiment of the present invention, an image of that scattered light from the surface of a semiconductor wafer 2, which is generated by illumination from an illuminating unit 3, is sensed line by line. The scattered light is generated when the surface of the semiconductor wafer 2 has defects such as flaws.

A personal computer 50 sets those inclination angles of the illuminating unit 3 and an image sensing unit 4, which are best suited to sensing an image of the scattered light. In this setting, a bare wafer having flaws or a wafer having defects in a specific region is used as the angle setting semiconductor wafer 2.

Alternatively, a detecting unit (not shown) is used to detect defects on the angle setting semiconductor wafer 2, and the personal computer 50 sets optimum inclination angles of the illuminating unit 3 and the image sensing unit 4 for the defective region. In this case, it is also possible to classify the types (flaws, dust, and the like) of defects in advance, store the classification information in a storage unit 503, and allow the personal computer 50 to determine the type of defect detected by the detecting unit on the basis of the information stored in the storage unit 503 and set the inclination angle for each defect type. Consequently, only an image of the scattered light from a certain type of defect on the semiconductor wafer 2 can be sensed in defect inspection.

Although a semiconductor wafer is used as an object to be inspected in the seventh to 17th embodiments described above, a liquid crystal glass substrate can also be used.

In the present invention, a diffracted image sensitive to changes on the surface of an object to be inspected can be sensed, so defect detection with higher accuracy is possible. Also, in the present invention, an inclination angle at which the diffracted light exits can be set on the basis of information such as a pattern pitch on the surface of an object to be inspected. Therefore, diffracted images corresponding to the state of the surface of an actual object to be inspected can be obtained, so diverse objects can be inspected. Furthermore, in the present invention, diffracted images are sensed at the inclination angle of a portion where the contrast of the diffracted light is a maximum. Accordingly, good inspection images can be obtained, so high-sensitivity defect detection can be performed.

In the present invention as described above, an optimum angle of at least one of the illuminating side and the image sensing side when an image of the diffracted light is to be sensed can be automatically set. Also, in the present invention, an optimum angle of at least one of the illuminating side and the image sensing side is calculated by way of trial in accordance with the pattern pitch or the wavelength of illuminating light, and the corresponding information (e.g., the pattern pitch or the wavelength of illuminating light) is superposed and displayed on a graph which indicates the relationship between the angle and the diffracted light, obtained by actually irradiating an object to be inspected with the illuminating light. This can set a more practical diffracted light receiving angle. Furthermore, in the present invention, an optimum angle of the illuminating side or the image sensing side can be set in accordance with design data by interacting with an inspector. Hence, the present invention can handle a variety of objects to be inspected and can perform defect detection with higher detectivity.

Figure 18:
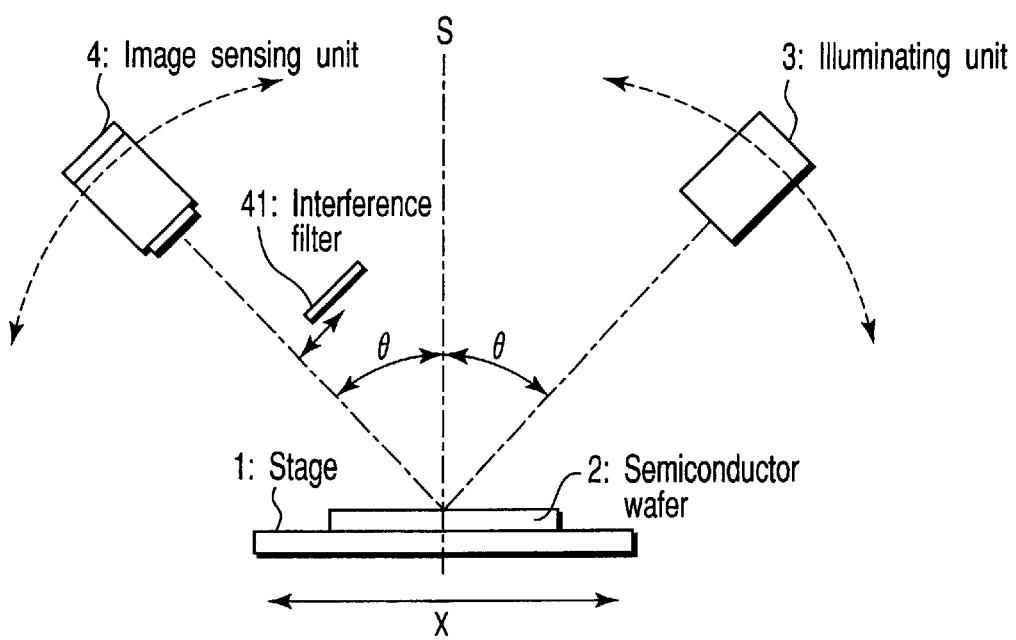
FIG. 18 is a view showing an outline of the configuration of an image sensing system and illuminating system of a defect detecting apparatus according to the 18th embodiment of the present invention.

FIG. 18 is a view showing an outline of the configuration of an image sensing system and illuminating system of a defect detecting apparatus according to the 18th embodiment of the present invention. Referring to FIG. 18, a semiconductor wafer 2 as an object to be inspected is placed on a stage 1. The stage 1 can move in the X direction. A linear illuminating unit 3 and an image sensing unit 4 such as a line sensor are arranged above the stage 1. The illuminating unit 3 obliquely irradiates the surface of the semiconductor wafer 2 with linear illuminating light. The illuminating unit 3 is so placed that an incident angle θ of the illuminating light with respect to a normal S passing the surface of the semiconductor wafer 2 is variable. The image sensing unit 4 senses line by line that interference observation image from the surface of the semiconductor wafer 2, which is generated by illumination by the illuminating unit 3. The image sensing unit 4 is so placed that an image sensing angle θ with respect to the normal S passing the surface of the semiconductor wafer 2 is variable.

Figure 19:
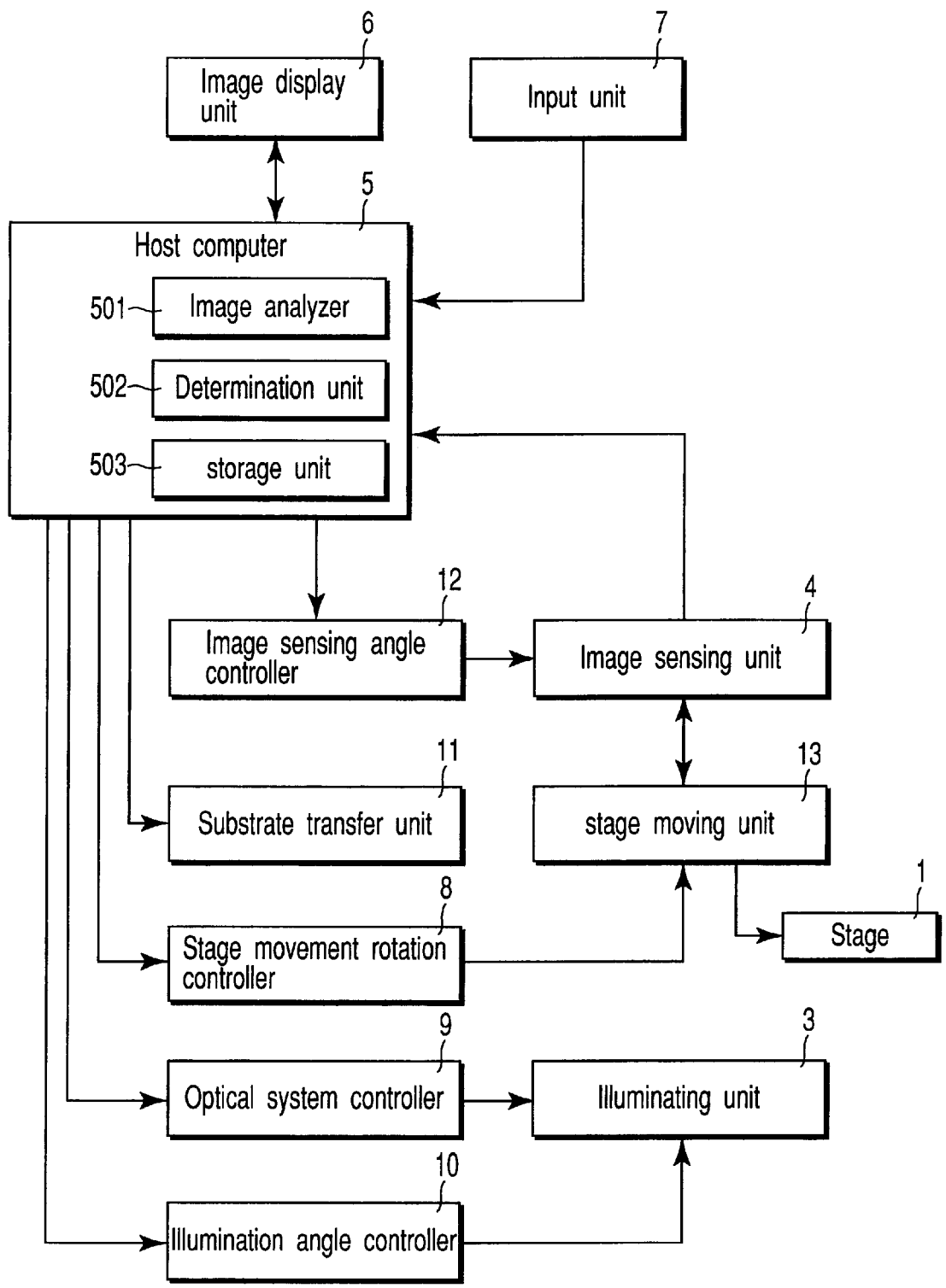
FIG. 19 is a view showing an outline of the configuration of a control system of the defect detecting apparatus according to the 18th embodiment of the present invention.

FIG. 19 is a view showing an outline of the configuration of a control system of the above defect detecting apparatus. Referring to FIG. 19, a host computer 5 is connected to the image sensing unit 4, an image display unit 6, an input unit 7, a stage movement rotation controller 8, an optical system controller 9, an illumination angle controller 10, a substrate transfer unit 11, and an image sensing angle controller 12. The illuminating unit 3 is connected to the optical system controller 9 and the illumination angle controller 10. The stage 1 and the image sensing unit 4 are connected to the stage movement rotation controller 8 via a stage moving unit 13. The image sensing unit 4 is connected to the image sensing angle controller 12. The host computer 5 has an image analyzer 501, a determination unit 502, and a storage unit 503. The image display unit 6 is a liquid crystal display or a CRT display. The input unit 7 is a keyboard or a mouse.

The host computer 5 executes a series of control operations for loading each one-line image signal from the image sensing unit 4, and processing the image signal to inspect defects of the semiconductor wafer 2. The image analyzer 501 loads and reconstructs each one-line image signal output from the image sensing unit 4. The image analyzer 501 then analyzes the reconstructed image data to extract defects such as film thickness variations, dust, and flaws on the semiconductor wafer 2, and causes the image display unit 6 to display information such as the types, numbers, positions, and areas of these defects.

On the basis of input conditions from the input unit 7, the determination unit 502 calculates an optimum angle (optimum interference angle) θ (=the incident angle θ of the illuminating light, the image sensing angle θ of the image sensing unit (the image sensing angle of the interference light)) for sensing an interference observation image by $$\theta 1=\sin^{-1}(n\cdot\sin(\cos^{-1}((2n\cdot d)/\lambda)))$$

$$\theta 2=\sin^{-1}(n\cdot\sin(\cos^{-1}((n\cdot d)/\lambda)))$$

$$\theta=\theta 1+(\theta 1-\theta 2)/2 \qquad (3)$$

Figure 20:
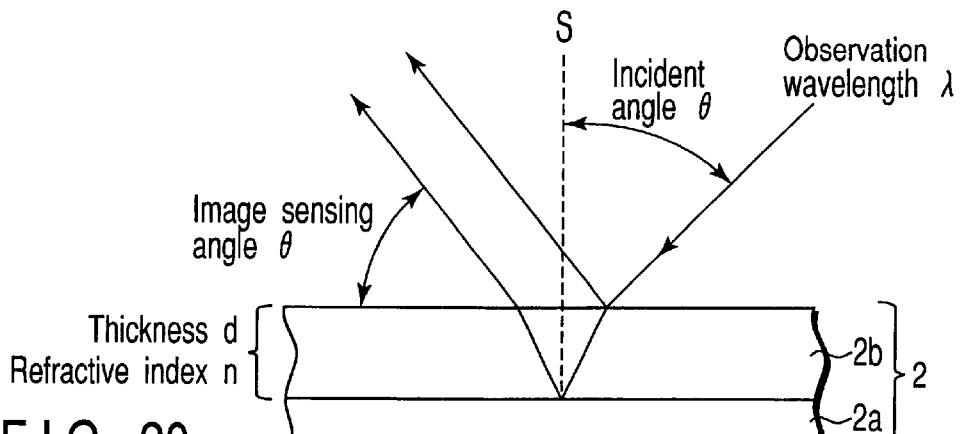
FIG. 20 is a view showing the relationship between the incidence angle of illuminating light to a resist film and the image sensing angle according to the 18th embodiment of the present invention.

As shown in FIG. 18, θ is the incident angle of the illuminating light emitted from the illuminating unit 3, θ is the image sensing angle of the image sensing unit 4, and λ is the observation wavelength when the image sensing unit 4 performs image sensing. Furthermore, as shown in FIG. 20, when a single-layer resist film 2b is formed on a substrate 2a of the semiconductor wafer 2, let d and n be the thickness and the refractive index, respectively, of the resist film 2b. The determination unit 502 sends the calculated optimum interference angle θ to the image sensing angle controller 12 and the illumination angle controller 10.

The image sensing angle controller 12 receives the optimum interference angle θ from the determination unit 502, and controls the movement of the image sensing unit 4 such that the image sensing angle becomes the optimum interference angle θ. The substrate transfer unit 11 controls a transfer section (not shown) in order to pick up semiconductor wafers 2 one by one from a storage stocker (cassette, not shown), place the semiconductor wafer 2 on the stage 1, and after defect inspection, return the semiconductor wafer 2 on the stage 1 to the stocker.

The stage movement rotation controller 8 drives the stage moving unit 13 for moving the stage 1 in, e.g., the X direction, in synchronism with image sensing by the image sensing unit 4, thereby controlling the movement, rotation, and positioning of the stage 1 having the semiconductor wafer 2 placed on it. To acquire an interference observation image, the optical system controller 9 controls the insertion of an interference filter 41 (not shown) and the light amount of the illuminating unit 3. The illumination angle controller 10 receives the optimum interference angle θ from the determination unit 502, and controls the movement of the illuminating unit 3 such that the incident angle of the illuminating light with respect to the surface of the semiconductor wafer 2 becomes the optimum interference angle θ.

The operation of the defect detecting apparatus configured as above will be described below.

When an inspector designates the start of inspection from the input unit 7, the host computer 5 displays, on the image display unit 6, a screen for requesting the input of the thickness d and the refractive index n (refer to FIG. 20) of the resist film 2b formed on the semiconductor wafer 2 to be inspected.

In accordance with this screen, the inspector inputs the thickness d and the refractive index n of the single-layer resist film 2b from the input unit 7. The determination unit 502 of the host computer 5 calculates the equation (3) by letting θ be the incident angle of the illuminating light emitted from the illuminating unit 3, θ be the image sensing angle of the image sensing unit 4, λ be the observation wavelength when the image sensing unit 4 performs image sensing, d be the thickness of the resist film 2b, and n be the refractive index of the resist film 2b. In this manner, the determination unit 502 obtains the optimum angle (optimum interference angle) θ for sensing an interference observation image, and sends the optimum interference angle θ to the image sensing angle controller 12 and the illumination angle controller 10.

The image sensing angle controller 12 receives the optimum interference angle θ from the determination unit 502, and controls the movement of the image sensing unit 4 such that the image sensing angle becomes the optimum interference angle θ. At the same time, the illumination angle controller 10 receives the optimum interference angle θ from the determination unit 502, and controls the movement of the illuminating unit 3 such that the incident angle of the illuminating light with respect to the surface of the semiconductor wafer 2 becomes the optimum interference angle θ. When the illuminating unit 3 and the image sensing unit 4 are thus set at the optimum interference angle θ, defect inspection for the semiconductor wafer 2 is started.

First, the inspector designates the start of defect inspection from the input unit 7. The substrate transfer unit 11 picks up a semiconductor wafer 2 from the stocker (not shown), and transfers and places the semiconductor wafer 2 onto the stage 1. The illuminating unit 3 emits illuminating light having the observation wavelength λ through the interference filter 41. As shown in FIG. 20, this illuminating light is reflected by the surface of the resist film 2b and also reaches the substrate 2a through the resist film 2b and is reflected by the surface of this substrate 2a. An interference observation image is generated by these reflected light components and incident on the image sensing unit 4.

From this state, the stage movement rotation controller 8 moves the stage 1 in the X direction at a constant velocity. In synchronism with this movement, the image sensing unit 4 senses the interference observation image line by line in a direction (Y direction) perpendicular to the moving direction of the stage 1. Each interference observation image sensed by the image sensing unit 4 is transferred to the image analyzer 501 of the host computer 5, until the entire surface of the semiconductor wafer 2 is completely scanned.

When interference images from the entire surface of the semiconductor wafer 2 are completely sensed after that, the image analyzer 501 analyzes these images. The image analyzer 501 loads and reconstructs each one-line image signal output from the image sensing unit 4, and analyzes the reconstructed image data to extract defects such as film thickness variations, dust, and flaws on the semiconductor wafer 2. The image analyzer 501 then obtains data such as the types, numbers, positions, and areas of these defects, and displays the data on the image display unit 6.

The semiconductor wafer 2 thus completely inspected is returned to the stocker by the substrate transfer unit 11. Subsequently, the substrate transfer unit 11 transfers an uninspected semiconductor wafer 2 from the stocker and places it on the stage 1.

In this 18th embodiment, on the basis of the thickness d and the refractive index n of the resist film 2b formed on the semiconductor wafer 2, the optimum interference angle θ for sensing interference observation images is calculated, and the illuminating unit 3 and the image sensing unit 4 are so controlled that the irradiation angle and the image sensing angle become the optimum interference angle θ. That is, the observation wavelength can be continuously changed by varying the irradiation angle and the image sensing angle, without selecting the observation wavelength step by step by interchanging a plurality of bandpass filters as in conventional apparatuses. Therefore, even when the interference conditions change owing to changes in the thickness d or the refractive index n of the resist film 2b of the semiconductor wafer 2 or the observation wavelength λ of the illuminating light, interference observation images can be sensed under most preferred conditions.

Outlines of the configuration of an image sensing system, an illuminating system and a control system of a defect detecting apparatus according to the 19th embodiment of the present invention are similar to those shown in FIGS. 18 and 19, respectively. In this 19th embodiment, the function of a determination unit 502 of a host computer 5 is different from that of the above 18th embodiment.

This 19th embodiment inspects defects on a semiconductor wafer 2 in which multilayered thin films different in refractive index are formed on a substrate 2a. Accordingly, unlike the 18th embodiment described above, the determination unit 502 of the host computer 5 has the following function.

Figure 21:
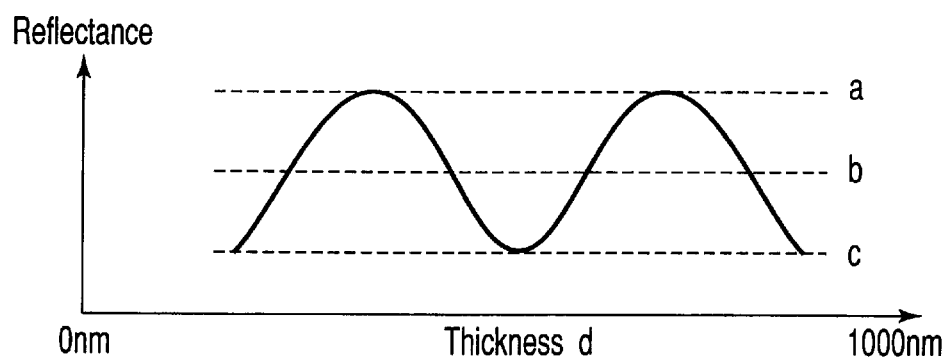
FIG. 21 is a graph showing the reflectance as a function of the thickness of a thin film according to the 19th embodiment of the present invention.

On the basis of input conditions from an input unit 7, the determination unit 502 calculates an optimum angle (optimum interference angle) θ (=the incident angle θ of illuminating light, the image sensing angle θ of an image sensing unit 4) for sensing an interference observation image, from the relationship (reflection graph), as shown in FIG. 21, between reflectance and a thickness d of the thin film.

As shown in FIG. 18, θ is the incident angle of the illuminating light emitted from an illuminating unit 3, θ is the image sensing angle of the image sensing unit 4, and λ is the observation wavelength when the image sensing unit 4 performs image sensing. Furthermore, when multilayered thin films, e.g., three films are formed on the substrate 2a of the semiconductor wafer 2, let $d_1$ and $n_1$ be the thickness and the refractive index, respectively, of the first thin film, $d_2$ and $n_2$ be the thickness and the refractive index, respectively, of the second thin film, and $d_3$ and $n_3$ be the thickness and the refractive index, respectively, of the third thin film. The determination unit 502 sends the calculated optimum interference angle θ to an image sensing angle controller 12 and an illumination angle controller 10.

The relationship (reflection graph) shown in FIG. 21 between reflectance and the thickness d of the thin film is a graph calculated when both the incident angle θ of the illuminating light and the image sensing angle θ of the image sensing unit 4 are 45°, the observation wavelength λ is 600 nm, and the refractive index n of the thin film is 1.5. In this reflection graph, in an uppermost portion a or a lowermost portion c of the curve, the change width of the reflectance due to a change in the film thickness is small, so the image luminance difference is small, i.e., the image saturates. Therefore, the determination unit 502 changes the angle θ or the observation wavelength λ, and sets the angle θ corresponding to a range including a middle portion b of the curve, as the optimum interference angle θ.

The operation of the defect detecting apparatus configured as above will be described below.

When an inspector designates the start of inspection from the input unit 7, the host computer 5 displays, on an image display unit 6, a screen for requesting the input of the thicknesses d and the refractive indices n of a plurality of thin films formed on the semiconductor wafer 2 to be inspected.

In accordance with this screen, the inspector inputs the thickness and the refractive index of each thin film from the input unit 7. When the number of thin films is three, for example, the inspector inputs the thickness $d_1$ and the refractive index $n_1$ of the first thin film, the thickness $d_2$ and the refractive index $n_2$ of the second thin film, and the thickness $d_3$ and the refractive index $n_3$ of the third thin film. The determination unit 502 of the host computer 5 calculates the optimum interference angle θ for sensing interference observation images. That is, the determination unit 502 changes the angle θ or the observation wavelength λ, and obtains the angle θ corresponding to the range including the middle portion b of the curve as the optimum interference angle θ, from the reflection graph of the reflectance as a function of the thin film thickness d as shown in FIG. 21. The determination unit 502 sends this optimum interference angle θ to the image sensing angle controller 12 and the illumination angle controller 10.

The image sensing angle controller 12 receives the optimum interference angle θ from the determination unit 502, and controls the movement of the image sensing unit 4 such that the image sensing angle becomes the optimum interference angle θ. At the same time, the illumination angle controller 10 receives the optimum interference angle θ from the determination unit 502, and controls the movement of the illuminating unit 3 such that the incident angle of the illuminating light with respect to the surface of the semiconductor wafer 2 becomes the optimum interference angle θ. When the illuminating unit 3 and the image sensing unit 4 are thus set at the optimum interference angle θ, defect inspection for semiconductor wafers 2 is started.

First, the inspector designates the start of defect inspection from the input unit 7. A substrate transfer unit 11 picks up a semiconductor wafer 2 as an object to be inspected from a stocker (not shown), and transfers and places the semiconductor wafer 2 onto a stage 1. The illuminating unit 3 emits illuminating light having the observation wavelength λ. The illuminating light is reflected by the surfaces of the plurality of thin films and also reaches the substrate through these thin films and is reflected by the surface of the substrate. An interference observation image is generated by these reflected light components and incident on the image sensing unit 4.

From this state, a stage movement rotation controller 8 moves the stage 1 in the X direction at a constant velocity. In synchronism with this movement, the image sensing unit 4 senses the interference observation image line by line in a direction (Y direction) perpendicular to the moving direction of the stage 1. Each interference observation image sensed by the image sensing unit 4 is transferred to an image analyzer 501 of the host computer 5, until the entire surface of the semiconductor wafer 2 is completely scanned.

When interference observation images from the entire surface of the semiconductor wafer 2 are completely sensed after that, the image analyzer 501 analyzes these images. The image analyzer 501 loads and reconstructs each one-line image signal output from the image sensing unit 4, and analyzes the reconstructed image data to extract defects such as film thickness variations, dust, and flaws on the semiconductor wafer 2. The image analyzer 501 then obtains data such as the types, numbers, positions, and areas of these defects, and displays the data on the image display unit 8.

The semiconductor wafer 2 thus completely inspected is returned to the stocker by the substrate transfer unit 11. Subsequently, the substrate transfer unit 11 transfers an uninspected semiconductor wafer 2 from the stocker and places it on the stage 1.

In this 19th embodiment, even when the interference conditions change owing to changes in the thickness or the refractive index of each of a plurality of thin films formed on the semiconductor wafer 2 or changes in the observation wavelength λ of the illuminating light, interference observation images can be sensed under most preferred conditions. The above explanation is based on the detection of changes in the uppermost thin film. However, images can be sensed under favored conditions in each layer. Additionally, defects generated only in an arbitrary layer can be detected by comparing the defect detection results of the individual layers.

Figure 22:
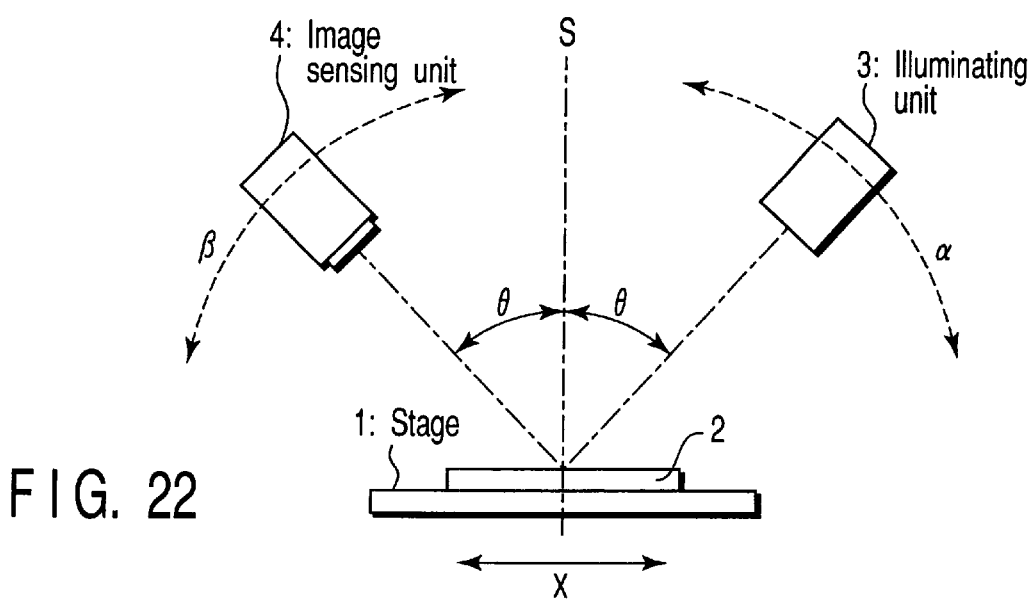
FIG. 22 is a view showing an outline of the configuration of an image sensing system and illuminating system of a defect detecting apparatus according to the 20th embodiment of the present invention.
Figure 23:
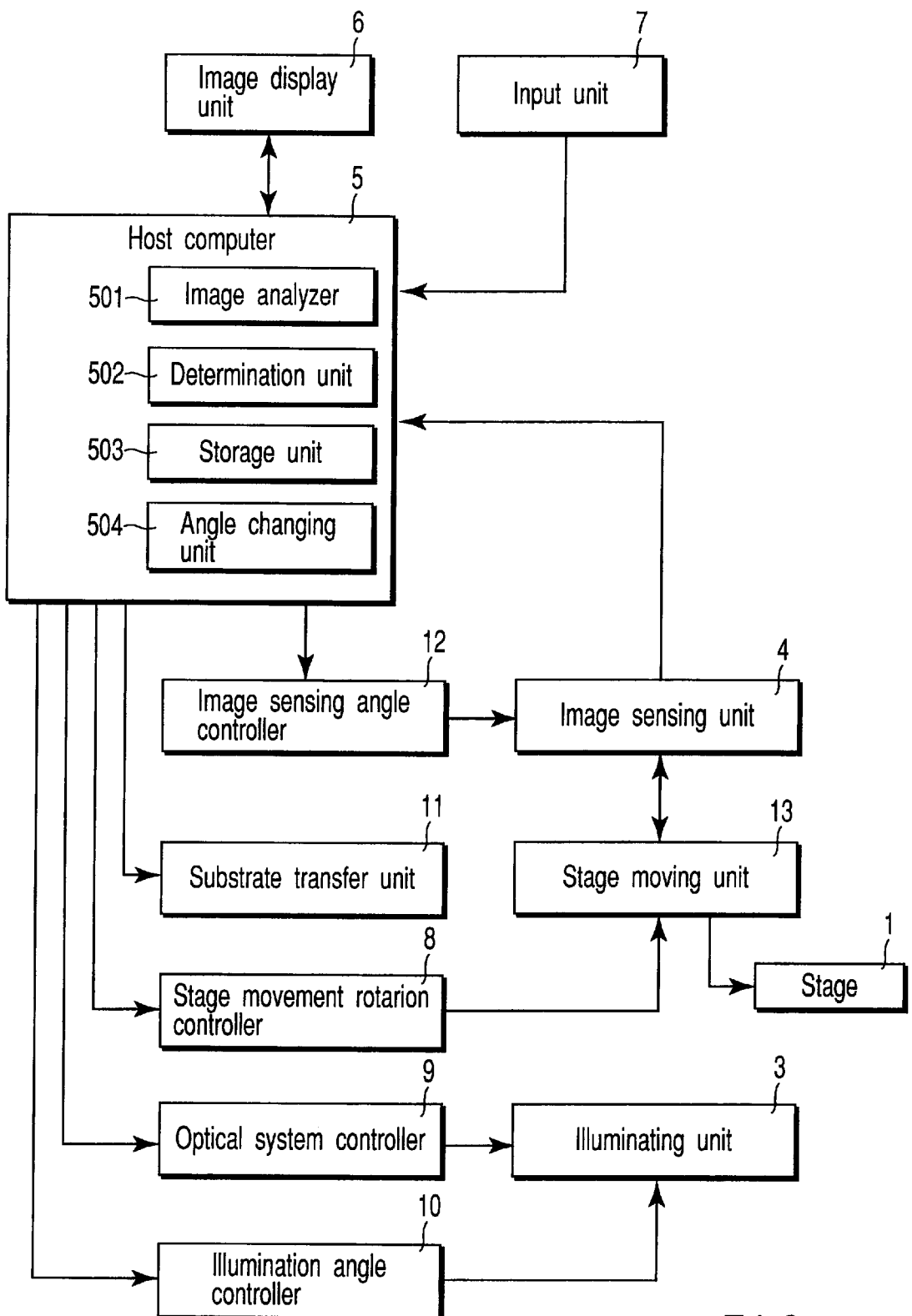
FIG. 23 is a view showing an outline of the configuration of a control system of the defect detecting apparatus according to the 20th embodiment of the present invention.

FIG. 22 is a view showing an outline of the configuration of an image sensing system and an illuminating system of a defect detecting apparatus according to the 20th embodiment of the present invention. FIG. 23 is a view showing an outline of the configuration of a control system of the defect detecting apparatus. In FIGS. 22 and 23, the same reference numerals as in FIGS. 18 and 19 denote the same parts.

Referring to FIG. 23, a host computer 5 has an image analyzer 501, a determination unit 502, a storage unit 503, and an angle changing unit 504. The host computer 5 has a function of automatically calculating an optimum interference angle θ in accordance with a flow chart, shown in FIG. 24, which indicates the procedure of setting the optimum interference angle, if a thickness d and a refractive index n of a resist film 2b formed on a semiconductor wafer 2 are unknown.

The angle changing unit 504 instructs a substrate transfer unit 11 to transfer and place a semiconductor wafer for setting an interference angle onto a stage 1 as shown in FIG. 22. The angle changing unit 504 then causes an image sensing angle controller 12 and an illumination angle controller 10 to rotate an image sensing unit 4 and an illuminating unit 3, respectively, in synchronism with each other at the same angle. That is, the angle changing unit 504 outputs a command to the image sensing angle controller 12 to move the image sensing unit 4 in the direction of an arrow β, and a command to the illumination angle controller 10 to move the illuminating unit 3 in the direction of an arrow α.

Figure 25:
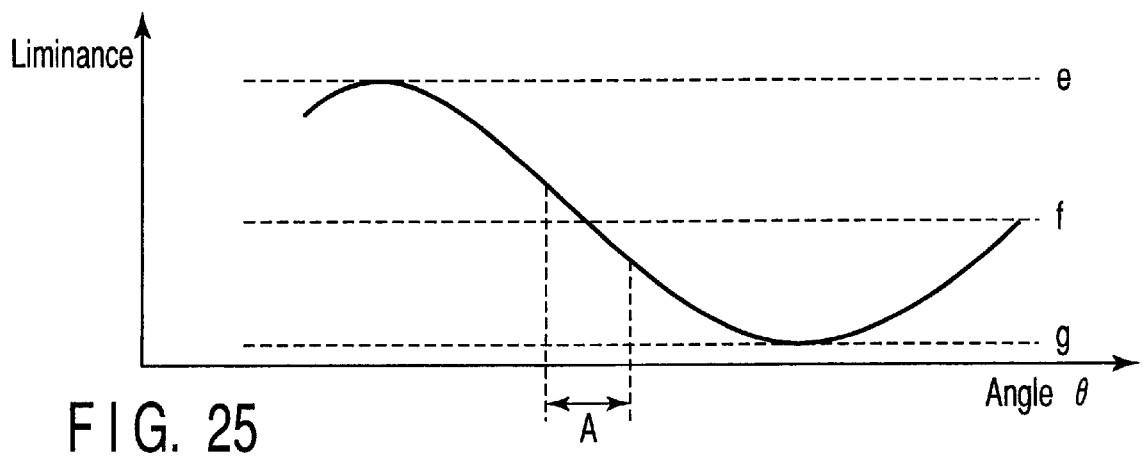
FIG. 25 is a graph showing the relationship between the luminance value and the illumination angle according to the 20th embodiment of the present invention.

The image analyzer 501 has a function of loading and reconstructing each one-line image signal output from the image sensing unit 4, when the illuminating unit 3 and the image sensing unit 4 thus simultaneously move through the same angle θ, and analyzing the reconstructed image data to obtain the relationship (interference luminance graph) between the angle θ and the luminance value as shown in FIG. 25. Note that when the illuminating unit 3 and the image sensing unit 4 simultaneously move through the same angle θ, the image analyzer 501 can also load each one-line image signal output from the image sensing unit 4, and obtain the interference luminance graph from the average of the image data of a predetermined number of lines.

The above-mentioned object for setting the interference angle is, e.g., a semiconductor wafer or a liquid crystal glass substrate in a fabrication lot, or is prepared for the purpose of setting the interference angle beforehand. An example of the object is a semiconductor wafer 2 in which a thin film or a plurality of thin films are formed on a substrate 2a. During the defect inspection of the semiconductor wafer 2, the image analyzer 501 loads and reconstructs each one-line image signal output from the image sensing unit 4, and analyzes the reconstructed image data to extract defects such as film thickness variations, dust, and flaws on the semiconductor wafer 2. The image analyzer 501 then obtains data such as the types, numbers, positions, and areas of these defects, and displays the data on an image display unit 6.

On the basis of the interference luminance graph obtained by the image analyzer 501, the determination unit 502 calculates the optimum interference angle θ (=the incident angle θ of the illuminating light, the image sensing angle θ of the image sensing unit 4) for sensing an interference observation image. The determination unit 502 sends the calculated optimum interference angle θ to the image sensing angle controller 12 and the illumination angle controller 10.

In the relationship between the angle θ and the luminance value shown in FIG. 25, in an uppermost portion e or a lowermost portion g of the curve, the change width of the reflectance due to a change of the resist film 2b is small, so the image luminance difference is small, i.e., the image saturates. That is, reflected light components enhance each other (white) in the uppermost portion e of the curve and weaken each other (black) in the lowermost portion g. Therefore, the determination unit 502 sets the angle θ corresponding to a range including a middle portion f of the curve, e.g., a range A, as the optimum interference angle θ.

The operation of the defect detecting apparatus configured as above will be described below.

Figure 24:
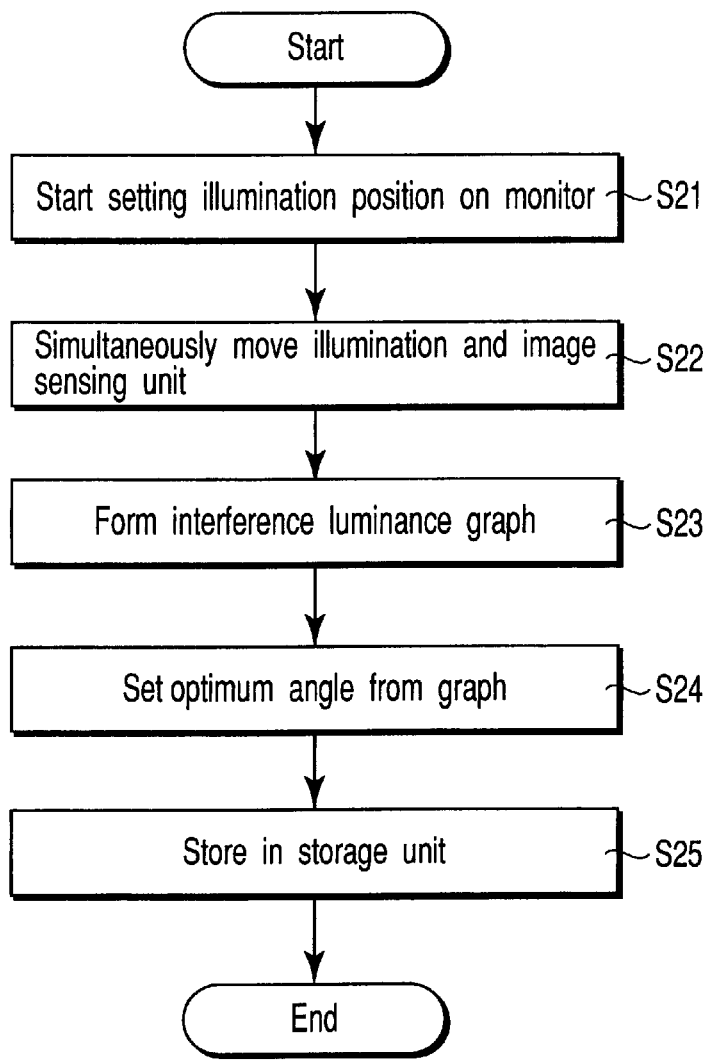
FIG. 24 is a flow chart showing the procedure of setting an optimum interference angle in the defect detecting apparatus according to the 20th embodiment of the present invention.

FIG. 24 is a flow chart showing the procedure of setting the optimum interference angle in the above defect detecting apparatus. First, an inspector designates the setting of the optimum interference angle from an input unit 7. In step S21, the host computer 5 outputs a command to the substrate transfer unit 11 to place a semiconductor wafer 2 for setting the interference angle on the stage 1. In response to this command, the substrate transfer unit 11 picks up the semiconductor wafer 2 from a stocker (not shown), and transfers and places it onto the stage 1. Subsequently, a stage movement rotation controller 8 positions the stage 1 on which the semiconductor wafer 2 is placed.

Next, in step S22, the angle changing unit 504 of the host computer 5 outputs a command to the image sensing angle controller 12 and the illumination angle controller 10 to move the image sensing unit 4 and the illuminating unit 3 in synchronism with each other at the same angle. As shown in FIG. 22, therefore, the illuminating unit 3 moves in turn in the direction of the arrow a to change the incident angle θ of the illuminating light. At the same time, the image sensing unit 4 moves in turn in the direction of the arrow β to change the image sensing angle θ at the same angle as the incident angle θ of the illuminating light. In this time, the stage 1 is at rest. While the incident angle θ of the illuminating light and the image sensing angle θ are simultaneously changing, the image sensing unit 4 senses interference observation images. The image sensing unit 4 transfers these interference observation images to the image analyzer 501 of the host computer 5, until the incident angle θ of the illuminating light and the image sensing angle θ are completely changed.

In step S23, the image analyzer 501 loads and reconstructs each one-line image signal output from the image sensing unit 4, when the illuminating unit 3 and the image sensing unit 4 simultaneously move at the same angle θ, and analyzes the reconstructed image data. The image analyzer 501 then obtains an interference luminance graph, as shown in FIG. 25, indicating the relationship between the luminance value and the angle θ to the semiconductor wafer 2 on which one or multilayered thin films are formed.

In step S24, on the basis of the interference luminance graph obtained by the image analyzer 501, the determination unit 502 obtains the angle θ corresponding to the range including the middle portion f of the curve shown in FIG. 25, e.g., the range A, as the optimum interference angle θ. The determination unit 502 sends the optimum interference angle θ to the image sensing angle controller 12 and the illumination angle controller 10. In step S25, the determination unit 502 stores the optimum interference angle θ in the storage unit 503.

The image sensing angle controller 12 receives the optimum interference angle θ from the determination unit 502, and controls the movement of the image sensing unit 4 such that the image sensing angle becomes the optimum interference angle θ. At the same time, the illumination angle controller 10 receives the optimum interference angle θ from the determination unit 502, and controls the movement of the illuminating unit 3 such that the incident angle of the illuminating light with respect to the surface of the semiconductor wafer 2 becomes the optimum interference angle θ. When the illuminating unit 3 and the image sensing unit 4 are thus set at the optimum interference angle θ, the substrate transfer unit 11 returns the semiconductor wafer 2 to the stocker, and defect inspection for the semiconductor wafer 2 is started.

First, the inspector designates the start of defect inspection from the input unit 7. The substrate transfer unit 11 picks up a semiconductor wafer 2 from the stocker (not shown), and transfers and places the semiconductor wafer 2 onto the stage 1. The illuminating unit 3 emits illuminating light having the observation wavelength λ. As shown in FIG. 20, this illuminating light is reflected by the surface of the resist film 2b, and also reaches the substrate 2a through the resist film 2b and is reflected by the surface of the substrate 2a. An interference observation image is generated by these reflected light components and incident on the image sensing unit 4.

From this state, the stage movement rotation controller 8 moves the stage 1 in the X direction at a constant velocity. In synchronism with this movement, the image sensing unit 4 senses the interference observation image line by line in a direction (Y direction) perpendicular to the moving direction of the stage 1. Each interference observation image sensed by the image sensing unit 4 is transferred to the image analyzer 501 of the host computer 5, until the entire surface of the semiconductor wafer 2 is completely scanned.

When interference observation images from the entire surface of the semiconductor wafer 2 are completely sensed after that, the image analyzer 501 analyzes these images. That is, the image analyzer 501 loads and reconstructs each one-line image signal output from the image sensing unit 4, and analyzes the reconstructed image data to extract defects such as film thickness variations, dust, and flaws on the semiconductor wafer 2 on which one or a plurality of thin films are formed. The image analyzer 501 then obtains data such as the types, numbers, positions, and areas of these defects, and displays the data on the image display unit 8.

The semiconductor wafer 2 thus completely inspected is returned to the stocker by the substrate transfer unit 11. Subsequently, the substrate transfer unit 11 transfers an uninspected semiconductor wafer 2 from the stocker and places the semiconductor wafer 2 on the stage 1.

In this 20th embodiment, if the thickness d and the refractive index n of the resist film 2b formed on the semiconductor wafer 2 are unknown, interference observation images are sensed by simultaneously changing the incident angle θ of the illuminating light and the image sensing angle θ. An interference luminance graph is obtained by analyzing the image data of these interference observation images, and the optimum interference angle θ is calculated from the interference luminance graph. Therefore, even when the thickness d and the refractive index n of the resist film 2b formed on the semiconductor wafer 2 are unknown, the optimum interference angle θ is automatically calculated. Accordingly, even when the interference conditions change owing to changes in the thickness d or the refractive index n of the resist film 2b of the semiconductor wafer 2 or the observation wavelength λ of the illuminating light, interference observation images can be sensed under preferred conditions.

As the semiconductor wafer 2 for setting the interference angle, a wafer in which one or multilayered thin films are formed on the substrate 2a is used. Hence, even when the semiconductor wafer 2 as an object to be inspected is a wafer on which one or multilayered thin films are formed, the optimum interference angle θ can be automatically calculated.

In each of the 18th to 20th embodiments described above, interference observation images are sensed by moving the stage 1 on which the semiconductor wafer 2 is placed. However, interference observation images can also be sensed by moving the illuminating unit 3 and the image sensing unit 4 together, while the stage 1 is at rest. Also, an object to be inspected is not restricted to a semiconductor wafer. For example, macroscopic defects such as film thickness variations, contamination, pattern step differences, and flaws on the surface of a liquid crystal glass substrate can be detected as well. Furthermore, the illuminating unit 3 can irradiate an object to be inspected such as a semiconductor wafer 2 with illuminating light having even illuminance at once, and the image sensing unit 4 can sense an image of the object at one time to acquire an interference observation image.

In the 21st embodiment, an appropriate interference filter 41 is inserted into an image sensing optical path in order to sense interference observation images corresponding to film thickness variations of a semiconductor wafer 2. For example, if an interference observation image is influenced by a layer such as a surface layer having large film thickness variations, a host computer 5 instructs an optical system controller 9 to insert the interference filter 41 having a wide wavelength band into the image sensing optical path. Alternatively, the optical system controller 9 removes the interference filter 41 from the image sensing optical path. Consequently, interference observation images unaffected by film thickness variations can be sensed. A similar effect can be obtained when the interference filter is installed in an illuminating unit 3.

A storage unit 503 of the host computer 5 stores, as design data, position information concerning those regions of the semiconductor wafer 2, which are objects of image sensing, together with information of the film thickness and refractive index. On the basis of the position information, the host computer 5 instructs the optical system controller 9 to control the interference filter 41 in accordance with the observation regions of the semiconductor wafer 2.

In the 22nd embodiment, the illuminating light is automatically adjusted in accordance with the state of a semiconductor wafer 2. An image analyzer 501 forms a graph indicating the frequency of a luminance value in a region to be inspected of a sensed image of the semiconductor wafer 2. For example, when the maximum luminance value (saturated luminance value) of this graph is 255, the host computer 5 causes an optical system controller 9 to adjust the illuminating light of an illuminating unit 3, such that the frequency is a maximum with a luminance value of 180. This light control is done by adjusting the internal lamp of the illuminating unit 3 or inserting an appropriate ND filter into an illuminating optical path. Also, the graph can be formed not only for an entire region to be inspected as a complete product, but also for a partial region to be inspected. Consequently, the illuminating light is adjusted in accordance with the state of an object to be inspected, so better image sensing results are obtained.

In the present invention as has been described above, interference observation images can be sensed under favored conditions.

The present invention is not limited to the above embodiments but can be practiced as it is properly modified without departing from the gist of the invention.

The present invention can provide a defect detecting apparatus capable of setting to an optimum state the angle of at least one of an illuminating side and an image sensing side with respect to an object to be inspected, and capable of treating various objects.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect detecting apparatus for extracting a defect from image data obtained by sensing an image of an object to be inspected, comprising:

an illuminating unit which irradiates said object with illumination from a direction of predetermined angle;

an image sensing unit which senses an image of said object from the direction of predetermined angle;

an angle controller which controls an inclination angle of at least one of said illuminating unit and said image sensing unit;

an image processor which senses images of said object while said angle controller changes the inclination angle of at least one of said illuminating unit and said image sensing unit and obtains a relationship between each inclination angle and optical information corresponding to said each inclination angle; and a determination unit which determines an image sensing condition suited to observation in accordance with the relationship between the inclination angle and optical information obtained by said image processor, wherein said angle controller sets the inclination angle of said illuminating unit or said image sensing unit on the basis of a determination result from said determination unit such that the inclination angle matches the image sensing condition.

2. A defect detecting apparatus according to claim 1, wherein said angle controller controls the inclination angle of at least one of said illuminating unit and said image sensing unit at an irradiation position set for each pattern region different in pattern on said object and sets the inclination angle of said illuminating unit or said image sensing unit such that the inclination angle matches the image sensing condition determined by said determination unit for each pattern region.

3. A defect detecting apparatus according to claim 2, wherein said object is placed on a rotary stage so that a direction of the pattern can be changed with respect to a line illumination direction of said illuminating unit.

4. A defect detecting apparatus according to claim 1, further comprising a display unit which displays an image of said object sensed by said image sensing unit and input means which designates the irradiation position on the image of said object displayed on said display unit, wherein the inclination angle of at least one of said illuminating unit and said image sensing unit is controlled at the irradiation position designated by said input means.

5. A defect detecting apparatus according to claim 4, wherein when said input means designates an irradiation position of at least one of row and column directions on chips regularly arrayed on said object, an irradiation position identical to the irradiation direction is automatically set for an nth chip in the row or column direction.

6. A defect detecting apparatus according to claim 1, wherein said angle controller sets different pattern regions on said object using design information, controls the inclination angle of at least one of said illuminating unit and said image sensing unit at the irradiation position set for each set pattern region, and sets the inclination angle of said illumination unit or said image sensing unit such that the inclination angle matches the image sensing condition determined by said determination unit for each pattern region.

7. A defect detecting apparatus according to claim 1, wherein said illuminating unit comprises a line illumination optical system which irradiates said object with line illumination, and said image sensing unit comprises a line sensor camera which senses an image on said object irradiated with said line illumination optical system and moves said object relative to said illuminating unit and said image sensing unit.

8. A defect detecting apparatus according to claim 1, wherein as the optical information obtained by said image processor, any statistical technique of an average value, maximum value, standard deviation, or the like of luminance values of diffracted light received by said image sensing unit is used.

9. A defect detecting apparatus according to claim 1, wherein the image sensing condition is an inclination angle of said illuminating unit or image sensing unit which optimally senses diffracted light, interference light, or scattered light.

10. A defect detecting apparatus according to claim 1, wherein said object is placed on a stage which moves forward and backward, and said image sensing unit senses images of said object while changing a moving direction of said stage so as to correspond to at least two of different observation conditions of diffracted light, interference light, and scattered light from said object.

11. A defect detecting apparatus according to claim 1, wherein the result from said determination unit is stored for each type of said object or for each fabrication step of said object.

12. A defect detecting apparatus according to claim 1, wherein said determination unit determines a position of nth-order light from a graph representing the relationship between the inclination angle and optical information obtained by said image processor.

13. A defect detecting apparatus according to claim 12, wherein said determination unit sets the inclination angle to a prestored reference inclination angle when said determination unit cannot determine the nth-order light in the graph.

14. A defect detecting apparatus according to claim 13, wherein the reference inclination angle is an inclination angle obtained by simulation or a previously set inclination angle.

15. A defect detecting apparatus according to claim 13, wherein the reference inclination angle is an angle shifted about 5 to 10° from a 45° position for obtaining a dark field image when the optical information is diffracted light.

16. A defect detecting apparatus according to claim 12, wherein an index for designating an inclination angle is superposed and displayed on the graph and displayed on a display unit to allow displaying or inputting an inclination angle and a pattern pitch value of said object on the same screen.

17. A defect detecting apparatus according to claim 1, wherein said determination unit selects, for a plurality of objects, an optimum graph from a plurality of graphs each representing the relationship between the inclination angle and optical information obtained by said image processor and determines a position of nth-order light from the selected graph.

18. A defect detecting apparatus according to claim 1, wherein said determination unit determines, for a plurality of objects, an inclination angle suited to observing a position of first-order light serving as an average value or maximum luminance value of the first-order light in accordance with a graph representing the relationship between the inclination angle and optical information obtained by said image processor.

19. A defect detecting apparatus according to claim 1, wherein said angle controller controls an inclination angle of at least one of said illuminating unit and said image sensing unit within a designated movable range including first-order light, and said determination unit determines a position of the first-order light from a graph representing the relationship between the inclination angle and optical information obtained by said image processor within the movable range.

20. A defect detecting apparatus according to claim 1, wherein said determination unit obtains a pitch pattern value, an order of diffracted light, an image sensing angle, or an illumination angle by $$\sin\theta d - \sin\theta i = m\lambda/p$$

θd: the image sensing unit inclination angle,

θi: the illuminating unit inclination angle, m: the order of diffracted light, and p: the pattern pitch.

21. A defect detecting apparatus according to claim 1, wherein said illuminating unit uses one of line illumination for illuminating said object in a line, one-time illumination for illuminating a whole surface of said object, and spot illumination for illuminating said object with a spot.

22. A defect detecting apparatus according to claim 1, wherein said defect detecting apparatus has a function of three-dimensionally driving said illumination unit or said image sensing unit, and said angle setting controller three-dimensionally drives said illumination unit or said image sensing unit to set an inclination angle having high directivity capable of sensing an image of diffracted light or interference light.

23. A defect detecting apparatus comprising:

an illuminating unit whose incident angle θ changes with respect to a normal to a surface of an object to be inspected;

an image sensing unit which senses an image of light reflected by said object illuminated with said illuminating unit, said image sensing unit has an image sensing angle θ changing with respect to the normal;

an image analyzer which extracts defect information from an image of said object sensed by said image sensing unit;

a determination unit which obtains an interference angle suited to interference observation on the basis of an observation wavelength and information concerning a film formed on said object; and an angle controller which controls an inclination angle of said illuminating unit and said image sensing unit on the basis of the interference angle obtained by said determination unit.

24. A defect detecting apparatus according to claim 23, wherein said determination unit calculates an optimum interference angle in accordance with a thickness and refractive index of said film.

25. A defect detecting apparatus according to claim 23, wherein said determination unit obtains an optimum interference angle in accordance with a relationship of a reflectance to a thickness of said film.

26. A defect detecting apparatus according to claim 23, wherein an angle corresponding to a range of large reflectances on a graph representing a relationship of a reflectance to a thickness of said film is obtained as an optimum interference angle.

27. A defect detecting apparatus according to claim 23, wherein an optimum interference angle corresponding to each layer is obtained in accordance with refractive indices and thicknesses of each film formed on said object.

28. A defect detecting apparatus comprising:

an illuminating unit whose incident angle θ changes with respect to a normal to a surface of an object to be inspected;

an image sensing unit which senses an image of light reflected by said object illuminated with said illuminating unit, said image sensing unit has an image sensing angle θ changing with respect to the normal;

an angle controller which controls said illuminating unit and said image sensing unit such that an incident angle to said object is set equal to an image sensing angle;

an image processor which causes said image sensing unit to sense an image while the inclination angle of said illumination unit and said image sensing unit is changed by said angle controller, thereby obtains a relationship of a luminance value to the inclination angle; and a determination unit which determines an optimum interference angle in accordance with the relationship of the luminance value to the inclination angle, which is obtained by said image processor, wherein said angle controller controls the inclination angle of said illuminating unit and said image sensing unit on the basis of the interference angle obtained by said determination unit.

* * * * *